US007196068B2

(12) United States Patent
Kim et al.

(10) Patent No.: US 7,196,068 B2
(45) Date of Patent: Mar. 27, 2007

(54) METHOD FOR TREATING CANCER USING P38/JTV-1 AND METHOD FOR SCREENING PHARMACEUTICAL COMPOSITION FOR TREATING CANCER

(75) Inventors: Sunghoon Kim, Seoul (KR); Bum-Joon Park, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 508 days.

(21) Appl. No.: 10/463,676

(22) Filed: Jun. 18, 2003

(65) Prior Publication Data

US 2004/0175375 A1 Sep. 9, 2004

(30) Foreign Application Priority Data

Mar. 3, 2003 (KR) .................... 10-2003-0013058

(51) Int. Cl.
*A01N 43/04* (2006.01)
*C12Q 1/68* (2006.01)
*C12N 15/64* (2006.01)
*C07H 21/02* (2006.01)
*C07H 21/04* (2006.01)

(52) U.S. Cl. .................. 514/44; 435/6; 435/91.1; 435/320.1; 435/455; 536/23.1; 536/23.2; 536/23.4; 536/23.5

(58) Field of Classification Search ............. 435/6, 435/91.1, 91.31, 455, 458, 375, 320.1; 514/1, 514/2, 44; 536/23.1, 23.2, 23.4, 23.5
See application file for complete search history.

(56) References Cited

U.S. PATENT DOCUMENTS 5,843,757 A * 12/1998 Vogelstein et al. ........ 435/252.3

OTHER PUBLICATIONS

Peracchi, A., Rev. Med. Virol., vol. 14, pp. 47-64 (2004).*
Branch, A., Trends in Biochem. Sci., vol. 23, pp. 45-50 (1998).*
Chirila, T.V. et al., Biomaterials, vol. 23, pp. 321-342 (2002).*
Agrawal, S. et al., Molecular Med. Today, vol. 6, pp. 72-81 (2000).*
S.T. Crooke, Antisense Res. & Application, Chapter 1, pp. 1-50 (S. Crooke, Ed.) (Publ. by Springer-Verlag) (1998).*
Quevillon, S. et al., "Macromolecular Assemblage of Aminoacyl-tRNA Synthetases: Identification of Protein-Protein Interactions and Characterization of a Core Protein," J. Mol. Biol., 1999, pp. 183-195, vol. 285.
Kolodner, R.D. et al., "Eukaryotic DNA mismatch repair," Curr. Opin. Gene. Dev., 1999, pp. 89-96, vol. 9.
Nicolaides, N.C. et al., "Analysis of the 5' Region of *PMS2* Reveals Heterogeneous Transcripts and a Novel Overlapping Gene," Genomics, 1995, pp. 329-334, vol. 29.
Duncan, R. et al., "A sequence-specific, single-strand binding protein activates the far upstream element of c-*myc* and defines a new DNA-binding motif," Genes and Development, 1994, pp. 465-480, vol. 8.

Avigan, M.I. et al., "A Far Upstream Element Stimulates c-*myc* Expression in Undifferentiated Leukemia Cells," J. Biol. Chem., Oct. 25, 1990, pp. 18538-18545, vol. 265, No. 30.
Kulik, G. et al., "Antiapoptotic Signalling by the Insulin-Like Growth Factor I Receptor, Phosphatidylinositol 3-Kinase, and Akt," Mol. Cell. Biol., Mar. 1997, pp. 1595-1606, vol. 17, No. 3.
Franke, T.F. et al., "P13K: Downstream AKTion Blocks Apoptosis," Cell, 1997, pp. 435-437, vol. 188, No. 4.
Kauffmann-Zeh, A. et al., "Suppression of c-Myc-induced apoptosis by Ras signaling through PI(3)K and PKB," Nature, Feb. 6, 1997, pp. 544-548, vol. 385.
Hemmings, B.A., "Akt Signalling—Linking Membrane Events to Life and Death Decisions," Science, Jan. 31, 1997, pp. 628-630, vol. 275, No. 5300.
Stokoe, D. et al., "Dual Role of Phosphatidylinositol-3,4,5-triphosphate in the Activation of Protein Kinase B," Jul. 25, 1997, pp. 567-570, vol. 277.
Stephens, L. et al., "Protein Kinase B Kinases That Mediate Phosphatidylinositol 3,4,5-Triphosphate-Dependent Activation of Protein Kinase B," Jan. 30, 1998, pp. 710-714, vol. 279.
Park, S.G. et al., "Precursor of Pro-apoptotic Cytokine Modulates Aminoacylation Activity of tRNA Synthetase," J. Biol. Chem., 1999, pp. 16673-16676, vol. 274, No. 24.
Wilson, J.M. et al., "Hepatocyte-directed Gene Transfer *in vivo* Leads to Transient Improvement of Hypercholesterolemia in Low Density Lipoprotein Receptor-deficient Rabbits," J. Biol. Chem., 1992, pp. 963-967, vol. 267, No. 2.
Wu, G.Y. et al., "Receptor-mediated Gene Delivery and Expression *in Vivo*," J. Biol. Chem., 1988, pp. 14621-14624, vol. 263, No. 29.
Miller, A.D., "Human gene therapy comes of age," Nature, Jun. 11, 1992, pp. 455-460, vol. 357.

(Continued)

*Primary Examiner*—Jane Zara
(74) *Attorney, Agent, or Firm*—Buchanan Ingersoll & Rooney PC

(57) ABSTRACT

The present invention relates to a method for treating cancer using p38/JTV-1 and a method for screening pharmaceutical composition for treating cancer. More particularly, this invention relates to the method for treating cancer, which comprises administering the effective amount of p38/JTV-1 protein or a nucleic acid encoding for said protein to the patient and the method for screening a pharmaceutical composition for treating cancer characterized by selecting a substance having an effect on the increase of the activity of the p38/JTV-1 protein and the intracellular level thereof.

The method according to the invention can be effectively used to treat cancer through the mechanism of suppressing the proliferation of cancer cells by binding to FBP (FUSE-binding protein) and thereby promoting the ubiquitination of FBP to downregulate c-myc gene, which is a proto-oncogene, and the mechanism of promoting the apoptosis of cells by binding to PDK-1 (phosphoinositide-dependent protein) and thereby inhibiting the phosphorylation of AKT (serine/threonine kinase). Also, p38/JTV-1 can be used as a target for screening of new anticancer agents, by virtue of such regulation mechanisms of p38/JTV-1.

8 Claims, 24 Drawing Sheets

OTHER PUBLICATIONS

Rosenfeld, M.A. et al., "*In Vivo* Transfer of the Human Cystic Fibrosis Transmembrane Conductance Regulator Gene to the Airway Epithelium," Cell, Jan. 10, 1992, pp. 143-155, vol. 68.

Lemarchand, P. et al., "Adenovirus-mediated transfer of a recombinant human $\alpha_1$-antitrypsin cDNA to human endothelial cells," Proc. Natl. Acad. Sci. USA, Jul. 1992, pp. 6482-6486, vol. 89.

Wolfe, J.H. et al., "Herpesvirus vector gene transfer and expression of $\beta$-glucuronidase in the central nervous system of MPS VII mice," Nature Genetics, Aug. 1992, pp. 379-384, vol. 1.

Kang, J. et al., "Heat Shock Protein 90 Mediates Protein-protein Interactions between Human Aminoacyl-tRNA Synthetases," J. Biol. Chem., Oct. 13, 2000, pp. 31682-31688, vol. 275, No. 41.

* cited by examiner

FIG. 5D

| p38/JTV-1 | FBP Binding | FBP Ubi | c-myc |
|---|---|---|---|
| 1 — 161 | + | + | + |
| 84 — 320 | + | + | + |
| 162 — 320 | − | − | − |
| 1 — 320 | + | + | + |

IP: FLAG

SEQUENCE LISTING

<160> NUMBER OF SEQ ID NOS: 17

<210> SEQ ID NO 1
<211> LENGTH: 936
<212> TYPE: DNA
<213> ORGANISM: Homo sapiens
<220> FEATURE:
<221> NAME/KEY: gene
<222> LOCATION: (1)..(936)
<223> OTHER INFORMATION: gene encoding 1-312 amino acid sequence of
      p38/JTV-1

<400> SEQUENCE: 1

| | | | | | |
|---|---|---|---|---|---|
| atgccgatgt | accaggtaaa | gccctatcac | gggggcggcg | cgcctctccg | tgtggagctt | 60 |
| cccacctgca | tgtaccggct | ccccaacgtg | cacggcagga | gctacggccc | agcgccgggc | 120 |
| gctggccacg | tgcaggaaga | gtctaacctg | tctctgcaag | ctcttgagtc | ccgccaagat | 180 |
| gatattttaa | aacgtctgta | tgagttgaaa | gctgcagttg | atggcctctc | caagatgatt | 240 |
| caaacaccag | atgcagactt | ggatgtaacc | aacataatcc | aagcggatga | gcccacgact | 300 |
| ttaaccacca | atgcgctgga | cttgaattca | gtgcttggga | aggattacgg | ggcgctgaaa | 360 |
| gacatcgtga | tcaacgcaaa | cccggcctcc | cctcccctct | ccctgcttgt | gctgcacagg | 420 |
| ctgctctgtg | agcacttcag | ggtcctgtcc | acggtgcaca | cgcactcctc | ggtcaagagc | 480 |
| gtgcctgaaa | accttctcaa | gtgctttgga | gaacagaata | aaaaacagcc | ccgccaagac | 540 |
| tatcagctgg | gattcacttt | aatttggaag | aatgtgccga | gacgcagat | gaaattcagc | 600 |
| atccagacga | tgtgccccat | cgaaggcgaa | gggaacattg | cacgtttctt | gttctctctg | 660 |
| tttggccaga | agcataatgc | tgtcaacgca | acccttatag | atagctgggt | agatattgcg | 720 |
| attttttcagt | taaaagaggg | aagcagtaaa | gaaaaagccg | ctgttttccg | ctccatgaac | 780 |
| tctgctcttg | ggaagagccc | ttggctcgct | gggaatgaac | tcaccgtagc | agacgtggtg | 840 |
| ctgtggtctg | tactccagca | gatcggaggc | tgcagtgtga | cagtgccagc | caatgtgcag | 900 |
| aggtggatga | ggtcttgtga | aaacctggct | cctttt | | | 936 |

<210> SEQ ID NO 2
<211> LENGTH: 483
<212> TYPE: DNA
<213> ORGANISM: Homo sapiens
<220> FEATURE:
<221> NAME/KEY: gene
<222> LOCATION: (1)..(483)
<223> OTHER INFORMATION: gene encoding 1-161 amino acid sequence of
      p38/JTV-1

<400> SEQUENCE: 2

| | | | | | |
|---|---|---|---|---|---|
| atgccgatgt | accaggtaaa | gccctatcac | gggggcggcg | cgcctctccg | tgtggagctt | 60 |
| cccacctgca | tgtaccggct | ccccaacgtg | cacggcagga | gctacggccc | agcgccgggc | 120 |
| gctggccacg | tgcaggaaga | gtctaacctg | tctctgcaag | ctcttgagtc | ccgccaagat | 180 |
| gatattttaa | aacgtctgta | tgagttgaaa | gctgcagttg | atggcctctc | caagatgatt | 240 |
| caaacaccag | atgcagactt | ggatgtaacc | aacataatcc | aagcggatga | gcccacgact | 300 |
| ttaaccacca | atgcgctgga | cttgaattca | gtgcttggga | aggattacgg | ggcgctgaaa | 360 |
| gacatcgtga | tcaacgcaaa | cccggcctcc | cctcccctct | ccctgcttgt | gctgcacagg | 420 |
| ctgctctgtg | agcacttcag | ggtcctgtcc | acggtgcaca | cgcactcctc | ggtcaagagc | 480 |
| gtg | | | | | | 483 |

-continued

<210> SEQ ID NO 3
<211> LENGTH: 687
<212> TYPE: DNA
<213> ORGANISM: Homo sapiens
<220> FEATURE:
<221> NAME/KEY: gene
<222> LOCATION: (1)..(687)
<223> OTHER INFORMATION: gene encoding 84-312 amino acid sequence of
      p38/JTV-1

<400> SEQUENCE: 3

```
gatgcagact tggatgtaac caacataatc caagcggatg agcccacgac tttaaccacc      60
aatgcgctgg acttgaattc agtgcttggg aaggattacg gggcgctgaa agacatcgtg     120
atcaacgcaa accggcctc ccctcccctc tccctgcttg tgctgcacag gctgctctgt      180
gagcacttca gggtcctgtc cacggtgcac acgcactcct cggtcaagag cgtgcctgaa     240
aaccttctca gtgctttgg agaacagaat aaaaaacagc cccgccaaga ctatcagctg      300
ggattcactt taatttggaa gaatgtgccg aagacgcaga tgaaattcag catccagacg     360
atgtgcccca tcgaaggcga agggaacatt gcacgtttct tgttctctct gtttggccag     420
aagcataatg ctgtcaacgc aacccttata gatagctggg tagatattgc gattttttcag    480 ttaaaagagg gaagcagtaa agaaaaagcc gctgttttcc gctccatgaa ctctgctctt     540
gggaagagcc cttggctcgc tgggaatgaa ctcaccgtag cagacgtggt gctgtggtct     600
gtactccagc agatcggagg ctgcagtgtg acagtgccag ccaatgtgca gaggtggatg     660
aggtcttgtg aaaacctggc tcctttt                                         687
```

<210> SEQ ID NO 4
<211> LENGTH: 312
<212> TYPE: PRT
<213> ORGANISM: Homo sapiens
<220> FEATURE:
<221> NAME/KEY: PEPTIDE
<222> LOCATION: (1)...(312)
<223> OTHER INFORMATION: 1-312 amino acid sequence of p38/JTV-1

<400> SEQUENCE: 4

```
Met Pro Met Tyr Gln Val Lys Pro Tyr His Gly Gly Gly Ala Pro Leu
  1               5                  10                  15

Arg Val Glu Leu Pro Thr Cys Met Tyr Arg Leu Pro Asn Val His Gly
             20                  25                  30

Arg Ser Tyr Gly Pro Ala Pro Gly Ala Gly His Val Gln Glu Glu Ser
         35                  40                  45

Asn Leu Ser Leu Gln Ala Leu Glu Ser Arg Gln Asp Asp Ile Leu Lys
     50                  55                  60

Arg Leu Tyr Glu Leu Lys Ala Ala Val Asp Gly Leu Ser Lys Met Ile
 65                  70                  75                  80

Gln Thr Pro Asp Ala Asp Leu Asp Val Thr Asn Ile Ile Gln Ala Asp
                 85                  90                  95

Glu Pro Thr Thr Leu Thr Thr Asn Ala Leu Asp Leu Asn Ser Val Leu
            100                 105                 110

Gly Lys Asp Tyr Gly Ala Leu Lys Asp Ile Val Ile Asn Ala Asn Pro
        115                 120                 125

Ala Ser Pro Pro Leu Ser Leu Leu Val Leu His Arg Leu Leu Cys Glu
    130                 135                 140

His Phe Arg Val Leu Ser Thr Val His Thr His Ser Ser Val Lys Ser
145                 150                 155                 160
```

```
Val Pro Glu Asn Leu Leu Lys Cys Phe Gly Glu Gln Asn Lys Lys Gln
                165                 170                 175
Pro Arg Gln Asp Tyr Gln Leu Gly Phe Thr Leu Ile Trp Lys Asn Val
            180                 185                 190
Pro Lys Thr Gln Met Lys Phe Ser Ile Gln Thr Met Cys Pro Ile Glu
        195                 200                 205
Gly Glu Gly Asn Ile Ala Arg Phe Leu Phe Ser Leu Phe Gly Gln Lys
    210                 215                 220
His Asn Ala Val Asn Ala Thr Leu Ile Asp Ser Trp Val Asp Ile Ala
225                 230                 235                 240
Ile Phe Gln Leu Lys Glu Gly Ser Ser Lys Glu Lys Ala Ala Val Phe
                245                 250                 255
Arg Ser Met Asn Ser Ala Leu Gly Lys Ser Pro Trp Leu Ala Gly Asn
            260                 265                 270
Glu Leu Thr Val Ala Asp Val Val Leu Trp Ser Val Leu Gln Gln Ile
        275                 280                 285
Gly Gly Cys Ser Val Thr Val Pro Ala Asn Val Gln Arg Trp Met Arg
    290                 295                 300
Ser Cys Glu Asn Leu Ala Pro Phe
305                 310

<210> SEQ ID NO 5
<211> LENGTH: 161
<212> TYPE: PRT
<213> ORGANISM: Homo sapiens
<220> FEATURE:
<221> NAME/KEY: PEPTIDE
<222> LOCATION: (1)...(161)
<223> OTHER INFORMATION: 1-161 amino acid sequence of p38/JTV-1

<400> SEQUENCE: 5

Met Pro Met Tyr Gln Val Lys Pro Tyr His Gly Gly Gly Ala Pro Leu
1               5                   10                  15
Arg Val Glu Leu Pro Thr Cys Met Tyr Arg Leu Pro Asn Val His Gly
            20                  25                  30
Arg Ser Tyr Gly Pro Ala Pro Gly Ala Gly His Val Gln Glu Glu Ser
        35                  40                  45
Asn Leu Ser Leu Gln Ala Leu Glu Ser Arg Gln Asp Asp Ile Leu Lys
    50                  55                  60
Arg Leu Tyr Glu Leu Lys Ala Ala Val Asp Gly Leu Ser Lys Met Ile
65                  70                  75                  80
Gln Thr Pro Asp Ala Asp Leu Asp Val Thr Asn Ile Ile Gln Ala Asp
                85                  90                  95
Glu Pro Thr Thr Leu Thr Thr Asn Ala Leu Asp Leu Asn Ser Val Leu
            100                 105                 110
Gly Lys Asp Tyr Gly Ala Leu Lys Asp Ile Val Ile Asn Ala Asn Pro
        115                 120                 125
Ala Ser Pro Pro Leu Ser Leu Leu Val Leu His Arg Leu Leu Cys Glu
    130                 135                 140
His Phe Arg Val Leu Ser Thr Val His Thr His Ser Ser Val Lys Ser
145                 150                 155                 160
Val

<210> SEQ ID NO 6
<211> LENGTH: 229
<212> TYPE: PRT
```

<213> ORGANISM: Homo sapiens
<220> FEATURE:
<221> NAME/KEY: PEPTIDE
<222> LOCATION: (1)...(229)
<223> OTHER INFORMATION: 84-312 amino acid sequence p38/JTV-1

<400> SEQUENCE: 6

```
Asp Ala Asp Leu Asp Val Thr Asn Ile Ile Gln Ala Asp Glu Pro Thr
 1               5                  10                  15
Thr Leu Thr Thr Asn Ala Leu Asp Leu Asn Ser Val Leu Gly Lys Asp
                20                  25                  30
Tyr Gly Ala Leu Lys Asp Ile Val Ile Asn Ala Asn Pro Ala Ser Pro
            35                  40                  45
Pro Leu Ser Leu Leu Val Leu His Arg Leu Leu Cys Glu His Phe Arg
50                  55                  60
Val Leu Ser Thr Val His Thr His Ser Ser Val Lys Ser Val Pro Glu
65                  70                  75                  80
Asn Leu Leu Lys Cys Phe Gly Glu Gln Asn Lys Lys Gln Pro Arg Gln
                85                  90                  95
Asp Tyr Gln Leu Gly Phe Thr Leu Ile Trp Lys Asn Val Pro Lys Thr
            100                 105                 110
Gln Met Lys Phe Ser Ile Gln Thr Met Cys Pro Ile Glu Gly Glu Gly
        115                 120                 125
Asn Ile Ala Arg Phe Leu Phe Ser Leu Phe Gly Gln Lys His Asn Ala
130                 135                 140
Val Asn Ala Thr Leu Ile Asp Ser Trp Val Asp Ile Ala Ile Phe Gln
145                 150                 155                 160
Leu Lys Glu Gly Ser Ser Lys Glu Lys Ala Ala Val Phe Arg Ser Met
                165                 170                 175
Asn Ser Ala Leu Gly Lys Ser Pro Trp Leu Ala Gly Asn Glu Leu Thr
            180                 185                 190
Val Ala Asp Val Val Leu Trp Ser Val Leu Gln Gln Ile Gly Gly Cys
        195                 200                 205
Ser Val Thr Val Pro Ala Asn Val Gln Arg Trp Met Arg Ser Cys Glu
    210                 215                 220
Asn Leu Ala Pro Phe
225
```

<210> SEQ ID NO 7
<211> LENGTH: 30
<212> TYPE: DNA
<213> ORGANISM: Artificial Sequence
<220> FEATURE:
<223> OTHER INFORMATION: Sense primer for p38/JTV-1

<400> SEQUENCE: 7
ccggaattca tgccgatgta ccaggtaaag                30

<210> SEQ ID NO 8
<211> LENGTH: 30
<212> TYPE: DNA
<213> ORGANISM: Artificial Sequence
<220> FEATURE:
<223> OTHER INFORMATION: Antisense primer for p38/JTV-1

<400> SEQUENCE: 8
ccgctcgagt taaaaggag ccaggttttc                 30

<210> SEQ ID NO 9

-continued

```
<211> LENGTH: 21
<212> TYPE: DNA
<213> ORGANISM: Artificial Sequence
<220> FEATURE:
<223> OTHER INFORMATION: Sense primer for p38/JTV-1

<400> SEQUENCE: 9
atgccgatgt accaggtaaa g                                           21

<210> SEQ ID NO 10
<211> LENGTH: 20
<212> TYPE: DNA
<213> ORGANISM: Artificial Sequence
<220> FEATURE:
<223> OTHER INFORMATION: Antisense primer for p38/JTV-1

<400> SEQUENCE: 10
aaaaggagcc aggttttcac                                             20

<210> SEQ ID NO 11
<211> LENGTH: 21
<212> TYPE: DNA
<213> ORGANISM: Artificial Sequence
<220> FEATURE:
<223> OTHER INFORMATION: Antisense primer for p38/JTV-1

<400> SEQUENCE: 11
cacgctcttg accgaggagt g                                           21

<210> SEQ ID NO 12
<211> LENGTH: 20
<212> TYPE: DNA
<213> ORGANISM: Artificial Sequence
<220> FEATURE:
<223> OTHER INFORMATION: Sense primer for p38/JTV-1

<400> SEQUENCE: 12
aaaccttctc aagtgctttg                                             20

<210> SEQ ID NO 13
<211> LENGTH: 21
<212> TYPE: DNA
<213> ORGANISM: Artificial Sequence
<220> FEATURE:
<223> OTHER INFORMATION: Sense primer for p38/JTV-1

<400> SEQUENCE: 13
agatgcagac ttggatgtaa c                                           21

<210> SEQ ID NO 14
<211> LENGTH: 20
<212> TYPE: DNA
<213> ORGANISM: Artificial Sequence
<220> FEATURE:
<223> OTHER INFORMATION: Sense primer for c-myc

<400> SEQUENCE: 14
cagcagcctc ccgcgacgat                                             20

<210> SEQ ID NO 15
<211> LENGTH: 20
<212> TYPE: DNA
<213> ORGANISM: Artificial Sequence
<220> FEATURE:
<223> OTHER INFORMATION: Antisense primer for c-myc

<400> SEQUENCE: 15
```

```
agcctggtag gaggccagct                                                    20

<210> SEQ ID NO 16
<211> LENGTH: 20
<212> TYPE: DNA
<213> ORGANISM: Artificial Sequence
<220> FEATURE:
<223> OTHER INFORMATION: Sense primer for GADPH

<400> SEQUENCE: 16
ttccatggca ccgtcaaggc                                                    20

<210> SEQ ID NO 17
<211> LENGTH: 20
<212> TYPE: DNA
<213> ORGANISM: Artificial Sequence
<220> FEATURE:
<223> OTHER INFORMATION: Antisense primer for GADPH

<400> SEQUENCE: 17
cttggcagcg ccagtagagg                                                    20
```

US 7,196,068 B2

METHOD FOR TREATING CANCER USING P38/JTV-1 AND METHOD FOR SCREENING PHARMACEUTICAL COMPOSITION FOR TREATING CANCER

FIELD OF THE INVENTION

The present invention relates to a method for treating cancer using p38/JTV-1 and a method for screening pharmaceutical composition for treating cancer. More particularly, this invention relates to the method for treating cancer, which comprises administering the effective amount of p38/JTV-1 protein or nucleic acid encoding for said protein to the patient and the method for screening the pharmaceutical composition for treating cancer characterized by selecting a substance having an effect on the increase of the activity of the p38/JTV-1 protein and the intracellular level thereof.

BACKGROUND OF THE INVENTION

Cancer refers to a cluster of cells showing overproliferation by non-coordination of the growth and proliferation of cells due to the loss of the differentiation ability of cells Most cancers occur by multistep carcinogenesis that the mutation of oncogenes and tumor suppressor genes occurs throughout 5~8 stages and finally cancer cells are generated. It has been known that activation of oncogenes inducing a cancer induces abnormal proliferation of cells and activation of tumor suppressor genes suppresses such abnormal proliferation of cells and blocks generation of cancer cells by killing specific cells by the activation of cell death program.

Until now, as genes associated with generation of cancer, there have been found 100 or more genes. Typical oncogenes include H-ras, N-ras, K-ras, c-myc and N-myc genes. These oncogenes are distributed throughout almost all the chromosomes in humans, and the mutation of these genes gives rise to abnormal proliferation of cells, which are then developed into cancer cells. Of them, the overexpression of c-myc was observed in various cancers in humans, for example, 80% of breast cancer, 70% of colon cancer, 90% of gynecological cancer and 50% of hepatocellular cancer. Besides, the abnormal overexpression of c-myc is known to be associated with blood tumor, cervical cancer, lung cancer, small cell lung cancer, stomach cancer, gonadal cancer, colon cancer, adenocarcinoma, promyelocyte leukemia, desmoplastic fibroblastoma, squamous cell carcinoma, myelocytoma and so on.

As typical tumor suppressor genes suppressing abnormal proliferation of cells, there can be mentioned p53, p16, p21, p24 and p27. The tumor suppressor genes suppress abnormal division and proliferation of cells and also, they have a function of repairing cellular DNAs when they are injured and have been known to be associated with regulation of apoptosis and proliferation of cells to prevent DNA from being amplified without limit.

Attempts to treat cancers using the oncogenes and tumor suppressor genes that have been recently identified are being under active progress. That is, various gene therapy including inhibition of the activity of oncogenes by developing compounds capable of downregulating the overexpressed oncogenes and by developing antisense genes against the oncogene, or in vivo replacement of the injured oncogenes by normal genes have been attempted. In addition, factors inducing the apoptosis of cancer cells have been developed in various manners as anticancer agents.

Meanwhile, p38/JTV-1 has been known as an auxiliary factor of aminoacyl-tRNA synthetases (ARSs) protein complex in higher eukaryotes (Quevillon S. et al., *J. Mol. Biol.,* 285; 183–195, 1999). Since the ARSs are enzymes catalyzing ligation of specific amino acid to their cognate tRNA, p3/JTV-1 is assumed to have a function associated with synthesis of proteins Besides, the gene coding for p38/JTV-1 is located in human chromosome 7 and arranged in a head to bead fashion with the gene coding for PMS2 that is involved in mismatch DNA repair (Kolodner R. D. et al., *Curr. Opin. Gene. Dev,* 9:89–96, 1999) The p38/JTV-1 protein that is coded by the p38/JTV-1 gene comprises 320 amino acid residues in mouse and comprises 312 amino acid residues in human, and their sequences have been known (Quevillon S. et al., *J. Mol. Biol.,* 285:183–195, 1999). The p38/JTV-1 protein is a hydrophobic protein and is assumed to contain leucine-zipper motif, which is a region associated with protein-protein interaction (Quevillon S. et al., *J Mol. Biol.* 8:285(1), 183–95, 1999) The p38/JTV-1 was also reported as another name, JTV-1 protein (Nicolaides et al., *Genomics,* 29:329–334, 1995). However, so far the exact functions of p38/JTV-1 have not been known.

The inventors of the present invention found that in the course of conducting the experiments to identify, the functions of p38/JTV-1, the p38/JTV-1 bound to the FBP (FUSE binding protein) that promotes the transcription of c-myc and bound to the PDK-1 (phosphoinositide-dependent kinase) in the AKT-P13K pathway of regulating apoptosis. Based on such findings, the inventors identified that the p38/JTV-1 has new activities of suppressing the proliferation of cells by downregulating c-myc through the interaction with FBP and of promoting apoptosis by suppressing phosphorylation of AKT (serin/threonine kinase) through the interaction with PDK-1 and also identified that the p38/JTV-1 could be useful as a tumor suppressor by virtue of such characteristics and accordingly, the inventors have completed the subject invention.

SUMMARY OF THE INVENTION

Therefore, the object of the present invention is to provide a method for downregulation of c-myc by promoting the ubiquitination of FBP, which comprises administering the effective amount of (a) an isolated p38/JTV-1 protein or fragment thereof, or (b) an isolated nucleic acid encoding said protein or fragment thereof to a patient.

Another object of the invention is to provide a method for promoting apoptosis of cell by suppressing the phosphorylation of AKT, which comprises administering the effective amount of (a) an isolated p38/JTV-1 protein or fragment thereof, or (b) an isolated nucleic acid encoding said protein or fragment thereof to a patient.

Another object of the invention is to provide a method for treating cancer, which comprises administering the effective amount of (a) an isolated p38/JTV-1 protein or fragment thereof, or (b) an isolated nucleic acid encoding said protein or fragment thereof to a patient.

Another object of the invention is to provide a method for screening a pharmaceutical composition for treating cancer characterized by selecting a substance having an effect on the increase of the activity of the p38/JTV-1 protein and the intracellular level thereof.

BRIEF DESCRIPTION OF THE DRAWINGS

FIG. 5d shows the FBP binding ability, the ubiquitination of FBP and the regulation of c-myc of p38/JTV-1 deletion fragments.

DETAILED DESCRIPTION OF THE INVENTION

Figure 1:
FIG. 1 shows the results of yeast two hybrid assay for the selection of cell proteins that interact with p38/JTV-1 (blue colony: positive interaction)

In order to achieve the aforementioned object, the present invention provides the method for downregulation of c-myc by promoting the ubiquitination of FBP, which comprises administering the effective amount of (a) an isolated p38/JTV-1 protein or fragment thereof; or (b) an isolated nucleic acid encoding said protein or fragment thereof to a patient.

Also, to achieve another object of the invention, the invention provides the method for promoting apoptosis of cell by suppressing the phosphorylation of AKT, which comprises administering the effective amount of (a) an isolated p38/JTV-1 protein or fragment thereof or (b) an isolated nucleic acid encoding said protein or fragment thereof to a patient.

Also, to achieve another object of the invention, the invention provides the method for treating cancer, which comprises administering the effective amount of (a) an isolated p38/JTV-1 protein or fragment thereof: or (b) an isolated nucleic acid encoding said protein or fragment thereof to a patient.

Also, to achieve another object of the invention, the invention provides the method for screening a pharmaceutical composition for treating cancer characterized by selecting a substance having an effect on the increase of the activity of the p38/JTV-1 protein and the intracellular level thereof.

The invention will be further described in detail.

The inventors identified new functions of p38/JTV-1 gene that has been known to have a critical role in the activity and stability of the formation of aminoacyl-tRNA synthetases (ARSs), which have not been known so far. The inventors observed that all mice that are deficient in p38/JTV-1 gene died within two days from their birth and examined the cause of death in mice. As a result, they could identify that the deficiency of p38/JTV-1 gene did not have an effect on the synthesis of proteins but induced the overexpression of alveolar cells. Further, it was observed that in mice deficient in p38/JTV-1 gene, the number of cells killed by apoptosis was decreased in comparison with wild type mice (data not shown). In this respect, the inventors assumed that the p38/JTV-1 would have new functions that have not been known so far in connection with the inhibition of cell proliferation and apoptosis, as well as its already-known function as an auxiliary factor of ARSs.

To identify new functions of p38/JTV-1, the inventors screened proteins that bind to p38/JTV-1 using yeast two hybrid assay. As a result of the experiment, they observed that the p38/JTV-1 specifically interacted with FBP (FUSE-binding protein), that binds to single stranded far-upstream sequence element (FUSE) of located about 1.5 kb upstream from c-myc promoter (Duncan R. et al., *Genes Dev.*, 8, 465–480, 1994) (see FIG. 1). This interaction between the p38/JTV-1 and FBP could be identified further by affinity purification and immunoprecipitation (data not shown).

The FBP (Fuse-binding protein) has been known as a protein inducing the expression of c-myc by binding to FUSE located in the upstream of the activated c-myc promoter. Accordingly, the FBP is called DNA-binding regulator of c-myc expression (DROME) (M. I. Avigan et al., *J. Biol. Chem.*, 265, 18538–18545, 1990). Recently, it has been reported that the activity of FBP could be negatively regulated by FIR (FBP-interaction suppressor) (Liu J. et al., *Mol. Cell*, 5, 331–341, 2000). In this case, the FIR has been known to form a complex together with FBP on FUSE DNA to repress the activator-dependent expression of c-myc.

Hence, the inventors investigated which functions the interaction between p38/JTV-1 and FBP that was newly found in this invention would conduct in connection with the expression of c-myc using a p38/JTV-1 deficient mouse.

In an embodiment of the invention, proteins were extracted from lung tissues in a p38/JTV-1 deficient mouse and a wild type mouse and their immunoblotting was conducted using specific antibodies against FBP, p38/JTV-1 and c-myc. As a result, the level of FBP and c-myc were higher in the p38/JTV-1 deficient mutant mouse compared to those in the wild type mouse (see FIG. 2). From such results, it was assumed that p38/JTV-1 would have an effect on the reduction in the intracellular level of FBP and c-myc To confirm such assumption, the change in the intracellular level of FBP and c-myc according to the increase of the expression of p38/JTV-1 was examined in another embodiment of the invention As a result, the intracellular level of FBP and c-myc were decreased as the expression level of p38/JTV-1 was increased (see FIG. 3).

In another embodiment of the invention, whether p38/JTV-1 is mediated with the ubiquitination of FBP was investigated. As a result, it could be seen that the ubiquitination of FBP was associated with 26S proteasome and the p38/JTV-1 promoted the ubiquitination of FBP (see FIG. 4a and FIG. 4b).

Further, the inventors constructed p38/JTV-1 deletion fragments and investigated a region that interacts with FBP. As a result, it could be seen that the interaction of p38/JTV-1 and FBP was associated with the N-terminal region of p38/JTV-1. Also, it could be seen that the p38/JTV-1 fragment promoted the ubiquitination of FBP by binding to FBP and the expression of c-myc was thus suppressed (see FIG. 5a~FIG. 5d)

Further, in another embodiment of the invention, the effect of TGF-β 2 on the expression of p38/JTV-1 was examined. As a result, the expression of p38/JTV-1 was increased by the treatment of TGF-β 2 (see FIG. 6). Consequently, the present inventors could identify TGF-β 2→p38/JTV-1→FBP→c-myc regulation mechanism wherein TGF-β 2 increases the expression of p38/JTV-1 and the expressed p38/JTV-1 promotes the ubiquitination of FBP by binding to FBP and thus downregulates the expression of c-myc (see FIG. 7)

In addition, the present inventors found that in tissues isolated from a p38/JTV-1 deficient mouse, the number of cells showing apoptosis was significantly reduced as compared to that of a wild type mouse and tried to identify the relationship between p38/JTV-1 and apoptosis regulation mechanism.

As important mechanism of regulating the apoptosis of cells and the survival of cells in vivo, AKT-PI3K pathway has been known (Kulik et al., *Mol. Cell Biol.*, 17(3): 1595–1606, 1997; Franke et al, *Cell*, 188(4):435–437, 1997; Kauffmann-Zeh et al., *Nature*, 385(6616):544–548, 1997; Hemmings, *Science*, 275(5300)628–630, 1997). Survival factors of cells, for examples, platelet-derived growth factor (PDGF), neuron growth factor (NGF) and insulin-like growth factor-1 (IGF-1) induce the activity of PI3K. The activated PI3K induces generation of phosphatidylinositol (3,4,5)-triphosphate (PtdIns(3,4,5)-P3), and the PtdIns(3,4,5)-P3 binds to AKT that is a serine/threonine kinase and then causes the translocation of AKT from cytoplasm to cellular membrane Due to this, phosphorylation occurs at threonine at 308th amino acid residue (Thr308) and serine at 473rd amino acid residue (Ser473) of AKT. The phosphorylated AKT inhibits apoptosis and promotes survival of cells. Recently, a protein kinase PDK-1 functioning as phosphorylating the Thr308 was identified, but a kinase phosphorylating Ser473 has not yet been identified (Stokeo et al., *Science*, 277:567–570, 1997; Stephens et al., *Science*, 279: 710–714, 1998).

Hence, to examine the relationship between p38/JTV-1 and AKT-PI3K pathway, in one embodiment of the invention, the inventors isolated several tissues from a p38/JTV-1 deficient mouse and investigated the expression level of the phosphorylated AKT and PI3K using western blotting. As a result, the expression level of PI3K and the total AKT in a p38/JTV-1 deficient mouse showed no differences from the wild type mouse whereas the expression of the phosphorylated AKT (p-AKT) in a p38/JTV-1 deficient mouse was increased as compared to that of the wild type mouse (see FIG. 8a and FIG. 8b).

To more concretely examine the relationship between p38/JTV-1 and the activity of AKT, an increase in the expression of p38/JTV-1 in cancer cell lines and a change in the expression of factors associated with AKT-PI3K pathway over the lapse of time were investigated in another embodiment of the invention. As a result, when the expression of p38/JTV-1 was increased, the expression of the phosphorylated AKT (p-308 and p-473) and PDK-1 was reduced whereas the expression of Bcl-2 family members and the total AKT showed no change (see FIG. 9a). Also, the suppression of phosphorylation of AKT by the p38/JTV-1 was increased in time-dependent manner (see FIG. 9b). These results supported that the p38/JTV-1 is a new negative regulator on activation of AKT.

In another embodiment of the invention, the interaction between p38/JTV-1 and PDK-1 was examined through yeast two hybrid assay and immunoprecipitation. As a result, a strong interaction between p38/JTV-1 and PDK-1 was observed On the other hand, there was no interaction between p38/JTV-1 and P13K (see FIG. 10a and FIG. 10b).

Figure 11A:
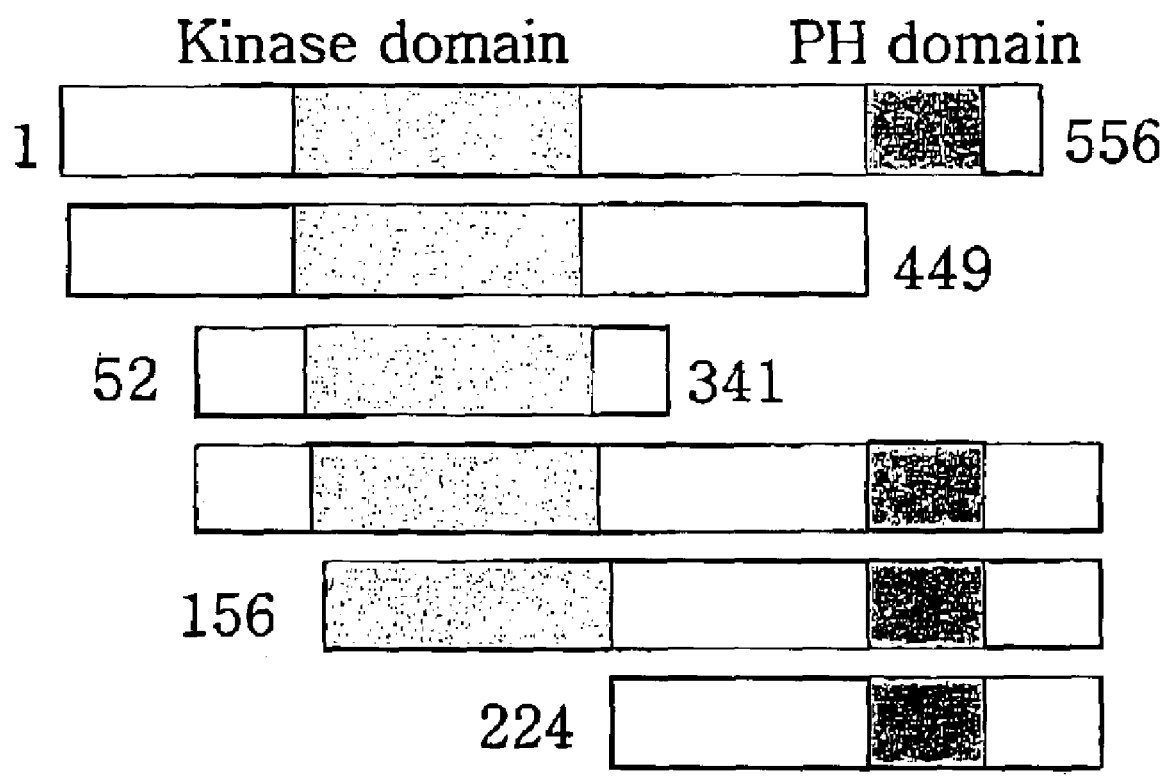
FIG. 11a is a scheme showing a PDK-1 deletion fragments comprising the kinase domain and the PH domain.

The interaction between p38/JTV-1 and PDK-1 could be confirmed by analyzing the tendency of the interaction between a PDK-1 deletion fragment and p38/JTV-1. That is to say, the p38/JTV-1 and PDK-1 whole fragment showed a strong interaction whereas when the kinase domain of PDK-1, which has an activity of phosphorylating AKT, was deleted, the remaining fragment and p38/JTV-1 showed no interaction (see FIG. 11a and FIG. 11b). From this, it could be said that the p38/JTV-1 blocked the phosphorylation of AKT by binding to the kinase domain of PDK-1.

In another embodiment of the invention, the expression level of p38/JTV-1 in cancer cell lines according to the treatment of FasL and TNF, which arc death ligands promoting apoptosis, was investigated. As a result, it was observed that according to the treatment of the death ligands, the expression of p38/JTV-1 was increased, phosphorylation of AKT was decreased due to the increase in the expression of the p38/JTV-1 and the interaction between p38/JTV-1 and PDK-1 was increased (see FIG. 12a and FIG. 12b)

Figure 13:
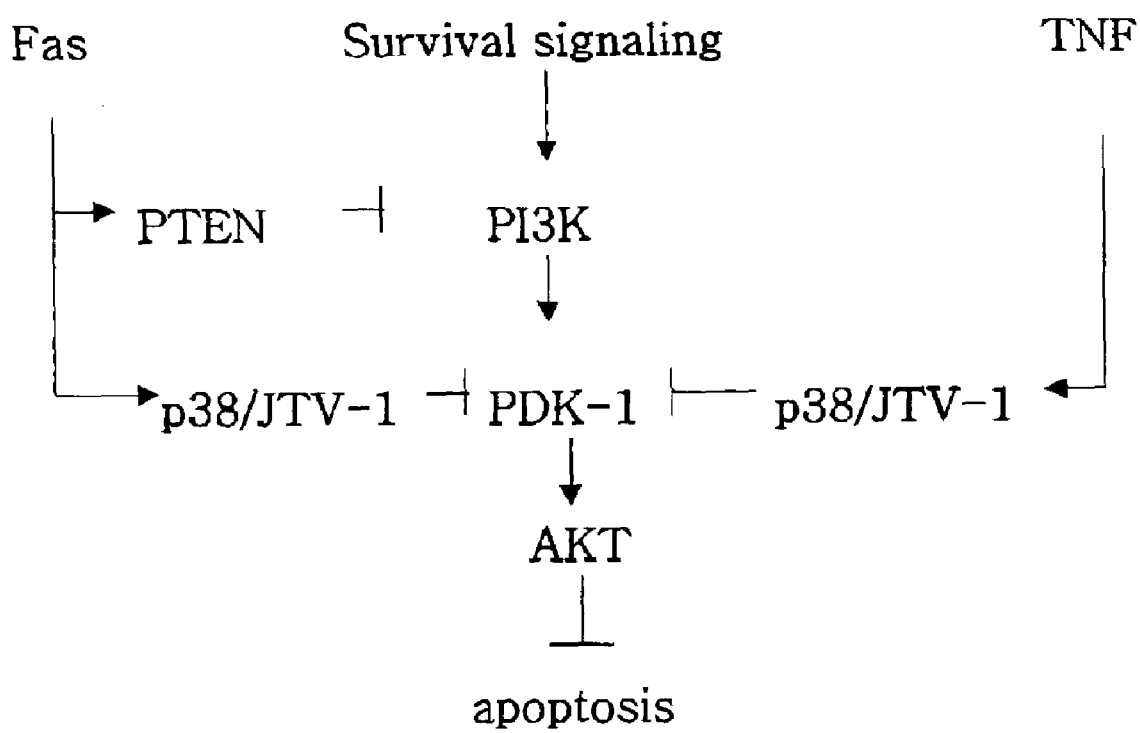
FIG. 13 is a scheme showing the regulation mechanism of apoptosis by p38/JTV-1 (arrow: promotion, T-shaped: suppression).

From the above experiment results, the present inventors newly found the mechanism that the expression of p38/JTV-1 is promoted by a death ligand and the expressed p38/JTV-1 suppresses the phosphorylation of AKT through the interaction with PDK-1, thereby promoting apoptosis (see FIG. 13).

Accordingly, the p38/JTV-1, which has been known merely as an auxiliary factor of ARSs, can be provided as a novel tumor suppressor promoting apoptosis as well as suppressing over-proliferation of cells through the interaction with the FBP and PDK-1. The inventors investigated the degree of apoptosis and the inhibitory degree of cell proliferation according to the increase of the expression of p38/JTV-1 in cancer cell lines, to confirm the use of p38/JTV-I as a tumor suppressor.

In an embodiment of the invention, the degree of cell proliferation was investigated by transfecting a human colorectal carcinoma cell line, cervical cancer cell line and lung epithelial carcinoma cell line with the p38/JTV-1 expression plasmid. As a result, it was observed that when the expression level of the p38/JTV-1 gene was increased, the proliferation of cancer cells was significantly suppressed (see FIG. 14).

Further, in another embodiment of the invention, the degree of release of cytochrome C and the degree of apoptosis of cells were determined by transfecting a cervical cancer cell line with a p38/JTV-1 expression plasmid. As a result, the degree of release of cytochrome C and apoptosis was increased within cells as compared with the case where the p38/JTV-1 gene was not introduced. Also, it could be seen that the apoptosis was increased by the treatment of the death ligand, TNF (see FIG. 15a and FIG. 15b). From this, it was confirmed that the p38/JTV-3 could be used as an anticancer agent by promoting apoptosis.

Therefore, the present invention provides the method for downregulation of c-myc by promoting the ubiquitination of FBP, which comprises administering the effective amount of (a) an isolated p38/JTV-1 protein or fragment thereof; or (b) an isolated nucleic acid encoding said protein or fragment thereof to a patient Also, to achieve another object of the invention, the invention provides the method for promoting apoptosis of cell by suppressing the phosphorylation of AKT, which comprises administering the effective amount of (a) an isolated p38/JTV-1 protein or fragment thereof, or (b) an isolated nucleic acid encoding said protein or fragment thereof to a patient.

Also, to achieve another object of the invention, the invention provides the method for treating cancer, which comprises administering the effective amount of (a) an isolated p38/JTV-1 protein or fragment thereof; or (b) an isolated nucleic acid encoding said protein or fragment thereof to a patient.

The p38/JTV-1 protein according to the present invention refers to natural or recombinant p38/JTV-1 protein, or the proteins with the substantially equivalent physiological activity The proteins with the substantially equivalent physiological activity include functional equivalents and functional derivatives of natural/recombinant p38/JTV-1 proteins.

The "functional equivalents" refer to those having a physiological activity substantially equivalent to the natural type p38/JTV-1 protein, as amino acid sequence modifiers wherein a part or all of the natural protein amino acids are substituted, or a part of the amino acids are deleted or added The "functional derivatives" refer to those having a physiological activity substantially equivalent to the natural type p38/JTV-1 protein, as proteins modified to increase or reduce the physicochemical properties of the p38/JTV-1 protein.

The p38/JTV-1 protein of the invention is derived preferably from mammals and more preferably, humans. The amino acid sequence of the p38/JTV-I protein was known (Genbank accession No. U24169)

Preferably, the p38/JTV-1 protein of the invention comprises amino acids represented by SEQ ID NO 4. The fragment of p38/JTV-1 protein comprises amino acids of amino acid 84 to 161 in SEQ ID NO. 4. More preferably, said fragment comprises amino acids represented by SEQ ID NO. 5 or SEQ ID) NO. 6.

The p38/JTV-1 protein or fragment thereof can be formulated according to commonly-used methods into various dosage forms by further comprising a pharmaceutically acceptable carrier. The "pharmaceutically acceptable" carrier as used herein refers to a substance that is physiologically acceptable and does not give rise to allergy reactions such as gastrointestinal disorder, dizziness, etc. or reactions similar thereto when administered into humans. As the pharmaceutically acceptable carriers, in the case of oral administration, there may be used a binder, lubricant, disintegrant, excipient, solubilizer, dispersion agent, stabilizer, suspension agent, pigment and flavor, and in the case of injection agent, there can be used a buffer, preserver, analgesic agent, solubilizer, isotonic agent and stabilizer in a mixed form, and in the case of preparations for local administration, and there can be used a base, excipient, lubricant and preserver. The dosage form of the p38/JTV-1 protein or fragment thereof can be prepared in various manners by mixing it with the pharmaceutical acceptable carriers as mentioned above. For example, in the case of oral administration, it can be formulated into the form of tablet, troche, capsule, elixir, suspension, syrup, wafer, etc. and in the case of injection agent, it can be formulated into the form of unit dosage ampoule or multi dosage forms.

The p38/JTV-1 protein or fragment thereof is administered into humans and animals orally, or parenterally such as intravenously, subcutaneously, intranasally or intraperitoneally. The oral administration includes sublingual application. The parenteral administration includes injection methods such as subcutaneous injection, intramuscular injection and intravenous injection, and drip infusion.

An isolated nucleic acid encoding for the p38/JTV-1 protein or fragment thereof refer to DNA or RNA. Preferably, it means a DNA encoding for the p38/JTV-1 protein derived from mammals and more preferably, humans. The human p38/JTV-1 gene was known (Genbank accession No.: U24169).

Preferably, the nucleic acid of the invention comprises nucleotide sequence represented by SEQ ID NO. 1. And the nucleic acid encoding fragment of the p38/JTV-1 protein comprises nucleotide sequence of 250 to 483 in SEQ ID NO. 1. More preferably, the nucleic acid encoding fragment of the p38/JTV-1 protein comprises nucleotide sequence represented by SEQ ID NO. 2 or SEQ ID NO. 3.

Further, within the scope of the nucleic acid of the invention, there can be included nucleic acids having at least 80%, preferably 90%, and more preferably 95% or more sequence homology with the nucleic acid encoding for p38/JTV-1 protein or the nucleic acid comprising the complementary nucleotide sequence thereof.

In addition, the nucleic acid of the invention can be contained within expression vectors such as a plasmid or viral vector in order to administer the nucleic acid to human or mammal. The expression vectors can be introduced into target cells in the form of expression by various methods known in the pertinent art such as infection or transduction.

The plasmid expression vector is the gene transfer method approved by FDA that can be applied to humans and is a method of transferring a plasmid DNA directly to human cells (Nabel, E. G., et al., *Science*, 249:1285–1288, 1990). The plasmid DNA has an advantage of being homogeneously purified, unlike the viral vector. As the plasmid expression vector that can be used in the present invention, there can be used mammal expression plasmids known in the pertinent art. For example, they are not limited to, but typically include pRK5 (European Patent No. 307,247), pSV16B (International Patent Publication 91/08291 A) and pVL1392 (PharMingen). In an embodiment of the invention, pcDNA3 (Invitrogen) was used.

The plasmid expression vector comprising the nucleic acid according to the invention can be introduced into tumor cells by the methods known in the pertinent art, for example, transient transfection, micro injection, transduction, cell fusion, calcium phosphate precipitation, liposome-mediated transfection, DEAE Dextran-mediated transfection, polybrene-mediated transfection, electroporation, gene gun and other known methods of introducing DNA into cells (Wu et al., *J. Bio. Chem.*, 267:963–967, 1992; Wu and Wu, *J. Bio Chem.*, 263:14621–14624, 1988). Preferably, the transient transfection method may be used.

Also, the virus expression vector comprising the nucleic acid according to the invention is not limited to, but includes retrovirus, adenovirus, herpes virus and avipox virus.

The retroviral vector is constructed so that non-viral proteins can be produced by the viral vector within the infected cells by the elimination or modification of all the virus genes. The main advantages of the retroviral vector for gene therapy lie in the fact that a quantity of genes are transferred into replicative cells, the genes transferred into cell DNA are accurately integrated and continuous infection does not occur after the gene transfection (Miller, A. D., *Nature*, 1992, 357:455–460) The rotroviral vector approved by FDA is constructed using PA317 amphotropic retrovirus package cells (Miller, A. D. and Buttimore, C., *Molec. Cell Biol.*, 6:2895–2902, 1986).

As non-retroviral vectors, there is adenovirus as mentioned above (Rosenfeld, M. A., et al., *Cell*, 68:143–155, 1992; Jaffe, H. A. et al., *Nature Genetics*, 1:372–378, 1992; Lemarchand, P. et al., *Proc. Natl. Acad. Sci USA*, 89:6482–6486, 1992). The main advantages of the adenovirus lie in the fact that it can transfer a quantity of DNA fragments (36 kb genome) and it is capable of infecting non-replicative cells with a very high titer. Also, the herpes virus can be usefully used for human gene therapy (Wolfe, J. H., et al., *Nature Genetics*, 1:379–384, 1992). Besides, other known suitable viral vectors can be used.

The viral vector can be administered by the known methods. For example, it can be administered locally, pareterally, orally, intranasally, intravenously, intramuscularly, subcutaneously, or by other suitable means. Especially, the vector can be injected directly into the target cancer or rumor cells in an amount effective to treat the tumor cells of a target tissue. In particular, in the case of cancer or tumor present in body cavity such as eyes, gastrointestinal tract, genitourinary organs, lungs and bronchus system, the pharmaceutical composition of the invention may be injected directly into the hollow organ affected by the cancer or tumor using a needle, catheter or other kinds of transfer tube. Image apparatus such as X-ray, sonogram or fiberoptic visualization system can be used for the confirmation of the location of the target tissue and the injection of needle or catheter. Besides, in the case of tumor or cancer that cannot be reached directly or separated by analyzation methods, the pharmaceutical composition according to the invention can be administered into blood circulation system.

Also, the nucleic acid according to the invention may further comprise pharmaceutically acceptable carriers or excipients. Such carriers or excipients include a dispersion agent, wetting agent, suspension agent, diluent and filler. The ratio of a specific, pharmaceutically acceptable carrier and the expression vector contained in the pharmaceutical composition of the invention may be determined by the solubility and chemical properties of the composition, specific administration method, etc.

The p38/JTV-1 protein or fragment and nucleic acid encoding thereof according to the invention can be administered to patient with the therapeutically or preventively effective amount and thereby treatment of cancer. The therapeutically or preventively effective amount can be suitably selected according to the subject to be administered, age, individual variation and disease conditions.

A 'patient' described above refer to mammal including human, preferably a human diagnosed with the cancers. The above cancers are not limited to, but may be breast cancer, large intestinal cancer, lung cancer, small cell lung cancer, stomach cancer, liver cancer, blood cancer, bone cancer, pancreatic cancer, skin cancer, head or neck cancer, cutaneous or intraocular melanoma, uterine sarcoma, ovarian cancer, rectal cancer, anal cancer, colon cancer, fallopian tube carcinoma, endometrial carcinoma, cervical cancer, vulval cancer, vaginal carcinoma, Hodgkin's disease, esophageal cancer, small intestine cancer, endocrine cancer, thyroid cancer, parathyroid cancer, adrenal cancer, soft tissue tumor, urethral cancer, penile cancer, prostate cancer, chronic or acute leukemia, lymphocytic lymphoma, bladder cancer, kidney cancer, ureter cancer, renal cell carcinoma, renal pelvic carcinoma, CNS tumor, primary CNS lymphoma, bone marrow tumor, brain stem nerve gliomas, pituitary adenoma, or a combination thereof.

Also, as the p38/JTV-1 has an activity of downregulating c-myc, which is a proto-oncogene, by binding to FBP and thereby promoting the ubiquitination of FBP and an activity of promoting apoptosis by binding to PDK-1 and thereby inhibiting the phosphorylation of AKT, as identified by the present invention, such characteristics of the p38/JTV-1 can be utilized to screen a substance effective for the treatment and prevention of cancer.

Accordingly, the present invention provides the method for screening a pharmaceutical composition for treating cancer characterized by comprising the steps of: (a) culturing a p38/JTV-1 protein or a recombinant cell expressing said protein with a candidate substance and (b) determining the effect of the candidate substance on the increase of the activity of the p38/JTV-1 protein or the intracellular level thereof. The increasing the activity of the p38/JTV-1 protein means the increase in the binding ability of the p38/JTV-1 protein to FBP protein or PDK-1. The increase in the intracellular level of the p38/JTV-1 protein means the increase in the concentration of the p38/JTV-1 protein by the increase of the expression of the p38/JTV-1 gene or the inhibition of the degradation of the p38/JTV-1 protein The expression of the p38/JTV-1 gene comprise the transcription of the p38/JTV-1 gene and translation procedure into protein. Accordingly, the candidate substances of the pharmaceutical composition for the treatment of cancer of the invention are those having characteristics of promoting the binding between the p38/JTV-1 and FBP or p38/JTV-1 and PDK-1, or increasing the intracellular level of the p38/JTV-1 protein.

As methods for determining the activity and intracellular level of the p38/JTV-1 protein, there can be used several methods known in the pertinent art. For example, they are not limited to, but include coimmunoprecipitation, enzyme-linked immuno sorbent assay, radioimmunoassay (RIA), immunohistochemistry, western blotting and fluorescence activated cell sorter (SACS) analysis.

Also, for the screening method using the p38/JTV-1 of the invention as a target gene, high throughput screening (HTS) can be applied. The HTS is the method of screening the biological activities of multiple candidate substances simultaneously or almost simultaneously by testing the multiple candidate substances at the same time. In a specific embodiment, cell lines are incubated in a 96-well microtiter plate or 192-well microtiter plate, into which multiple candidate substances are then treated and thereafter, the expression level of p38/JTV-1 can be determined by immunochemistry. In this format, 96 independent tests can be conducted at the same time on a single 8 cm×12 cm plastic plate containing 96 reaction wells. Typically, the well requires an assay volume ranging from 50 µl to 500 µl. Besides the plates, a number of instruments, apparatuses, pipettes, robots, plate washers and plate readers are available to adjust the 96-well format to broad homogeneous and heterogeneous assays.

The present invention will be further described in detail by the examples.

However, the following examples solely illustrate the invention; the matter of the invention should not be construed to be limited thereto.

Example 1

Regulation Mechanism of c-myc by the Interaction Between p38/JTV-1 and FPB

Example 1-1

Screening of Binding Proteins that Interact with p38/JTV-1 Using Yeast Two Hybrid Analysis As yeast two hybrid analysis, LexA system was used. Human p38/JTV-1 and LexA protein were fused and then expressed, and the p38/JTV-1 itself, lysyl-tRNA synthetase (KRS), FUSE-binding protein (FBP), tryptophanyl-tRNA synthetase (WRS) tyrosyl-tRNA synthetase (YRS) and glutaminyl-tRNA synthetases (QRS), respectively were fused with B42 protein and then expressed whereby proteins that interacted with the p38/JTV-1 protein were screened.

To express the fission protein of p38/JTV-1 and LexA, a recombinant plasmid, pLexA-(p38/JTV-1), into which p38/JTV-1 cDNA is introduced, was constructed. The p38/JTV-1 cDNA was obtained by a PCR amplification using the forward primer (SEQ ID NO. 7) and reverse primer (SEQ ID NO. 8) shown in Table 1 below, which were manufactured from the known nucleotide sequence of p38/JTV-1 cDNA (Gene Bank Accession No.: U24169) using human cervical cancer cell line HeLa cDNA library (Clontech) as a template. The above obtained cDNA of p38/JTV-1 was digested with EcoRI and SalI and subcloned into EcoRI and SalI sites of pLex202 vector (Invitrogen) to thereby construct pLexA-(p38/JTV-1). The PCR was performed 25 cycle with 1 min. at 94° C., 1 min. at 57° C. and 1 min. at 72° C. after the template DNA was denaturation with 94° C. for 5 min.

TABLE 1

Primers Used for the Amplification of p38/JTV-1 cDNA

| Primer | Sequence | SEQ ID NO. |
|---|---|---|
| p38/JTV-1 forward primer | CCGGAATTCATGCCGATGTACCAGGTAAAG | 7 |
| p38/JTV-1 reverse primer | CCGCTCGAGTTAAAAAGGAGCCAGGTTTTC | 8 |

To express the fusion protein of the binding proteins and B42, recombinant plasmids, pB42-(p38/JTV-1), pB42-FBP, pB42-KRS, pB42-WRS, pB42-YRS and pB42-QRS were constructed as follows The p38/JTV-1 cDNA prepared in the above was inserted into EcoRI and XhoI sites of pB42 vector (Invitrogen) to thereby construct the pB42-(p38/JTV-1) plasmid. The cDNA encoding the full-length human FBP (Gene Bank Accession No.: NM_003902) was provided by Dr. D. Levens (National Institutes of Health; NIH, USA), the fragment of amino acids from 564 to 645 at C-terminal region was inserted into EcoRI and XhoI sites to thereby construct the pB42-FBP plasmid. The cDNAs encoding KRS, WRS, YRS and QRS were obtained from digest of the LexA-KRS, LexA-WRS, LexA-YRS and LexA-QRS that the inventors constructed before (Kang J. W. et al., *J. Biol. Chem.*, 275:41, 31682–31688, 2000) with EcoRI and XhoI. The cDNAs were inserted into EcoRI and XhoI sites of pB42 to thereby construct pB42-KRS, pB42-WRS, pB42-YRS and pB42-QRS.

Using the recombinant plasmids constructed in the above, *Saccaromyces cerevisiae* EGY48 (Clontech laboratories Inc. Estojak et al. (1995)) having a lacZ plasmid (p8op-LacZ) as a probe gene was transformed according to the known methods (Golemis, E. A., et al., *In Current Protocols in Molecular Biology*, 1994). The interaction between LexA-(p38/JTV-1) and the binding proteins expressed as the B42-fusion forms were tested by culturing the tranformed yeast strains on the YPD plates containing X-gal (Rho S. B. et al., *Proc. Natl. Acad. Sci. USA* 96, 4488–4493, 1999). The positive interaction of LexA-(p38/JTV-1) and the binding proteins indicate by formation of blue colony.

As a result, the strong and positive interaction appeared in p38/JTV-1, KRS and FBP but no interaction appeared in tryptophanyl-WRS, tyrosyl-YRS and QRS (FIG. 1). The homodimerization of the p38/JTV-1 was already known, and it was also already known that the p38/JTV-1 specifically interacts with KRS. However, the fact that the p38/JTV-1 interacts with FBP was not reported before and was identified for the first time in the subject invention Example 1-2

Determination of the Intracellular Levels of FBP and c-myc in p38/JTV-1-Deficient Mutant Mouse Lung From wild type mouse (+/+), heterozygous mutant mouse, deficient in only one p38/JTV-1 allele (+/−) and homozygous mutant mouse, deficient in both p38/JTV-1 alleles (−/−), lungs were isolated, proteins were extracted from the lungs and then the proteins were western blotted with the anti-p38/JTV-1, anti-FBP and anti c-myc antibodies to thereby analyze the intracellular levels of FBP and c-myc As the wild type mouse (+/+) male C57B mouse (Samtako) on one-day-old was used. The p38/JTV-1 mutant mice were prepared according to the known methods (Kim et al., *Proc. Natl. Acad. Sci., USA*, 99:7912–7916).

From the wild type mouse and p38/JTV-1 mutant mice, lungs were isolated and proteins were extracted from the lungs. The lung tissues isolated from the mice were homogenized using a polytron homogenizer in 20 mM Tris buffer (pH 7.5). 10 mM NaCl, 0.5 mM EDTA and 0.5 mM phenylmethylsulonyl fluoride using a polytron homogenizer. The homogenate was centrifuged at 100,000 g for one hour and the supernatants (cytosolic fraction) was collected, into which adjusted to 0.5% Triton X-100 to extract cell proteins. The extracted proteins were western blotted using the anti-p38/JTV-1, anti-FBP and anti c-myc antibodies (Santa Cruz Biotechnology, USA) according to the known methods (Kim T. et al., *J. Biol. Chem.*, 275:21786–21772, 2000). The anti-tubulin antibody (Santa Cruz Biotechnology, USA) was used as the loading control.

Figure 2:
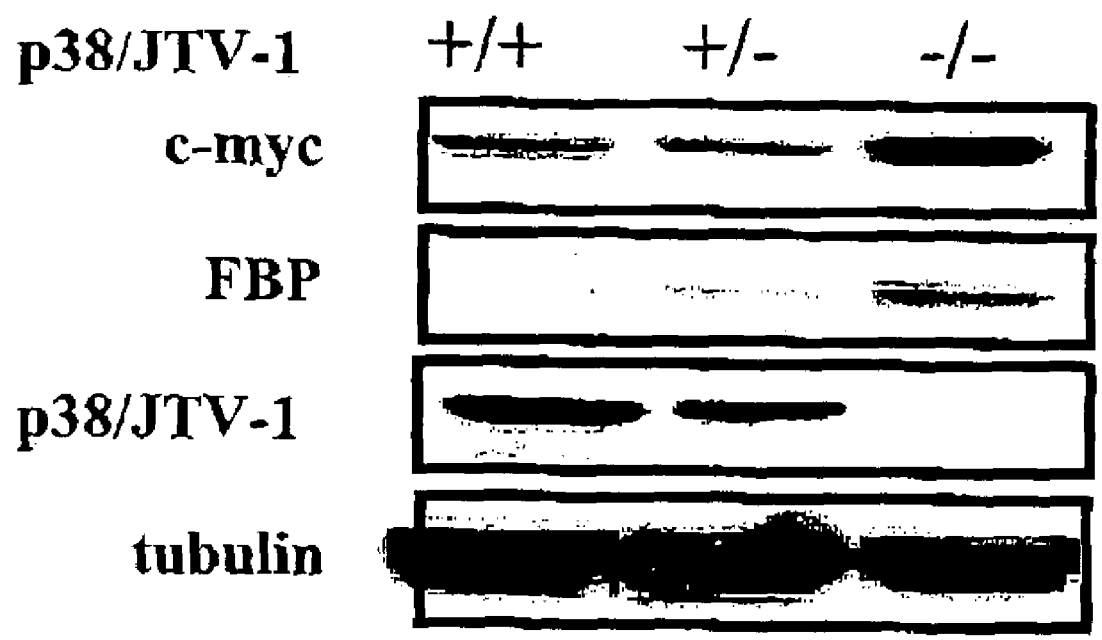
FIG. 2 is the western blotting results showing the levels of c-myc, FBP and p38/JTV-1 in the lungs of wild type mouse and p38/JTV-1 deficient mutant mouse. Tubulin was used as the loading control (+/+ wild type mouse, +/− heterozygous mutant mouse, and −/− homozygous mutant mouse)

As a result, the levels of FBP and c-myc were higher in the lungs of the p38/JTV-1 homoczygous mutant mouse (−/−) compared to those in the wild type mouse (+/+) or the p38/JTV-1 heterozygous mutant mouse (+/−) (FIG. 2). This result means that the p38/JTV-1 has an effect of reducing the levels of FBP and c-myc.

Example 1-3

Change in the Intracellular Levels of FBP and c-myc According to the Increase of the Expression of p38/JTV-1

The effect of the expression of p38/JTV-1 on the intracellular levels of FBP and c-myc was investigated by transfecting human embryonic kidney 293 cells (assigned from ATCC) with p38/JTV-1 plasmids having different amounts. The human embryonic kidney 293 cells were transfected with 0.5 µg/ml or 2 µg/ml of p38/JTV-1 expression plasmid and 2 µg/ml of FBP expression plasmid, respectively. The p38/JTV-1 expression plasmid was constructed by inserting the p38/JTV-1 cDNA of Example 1 subcloned into EcoRI-XhoI sites of myc-tagged pcDNA3 (Invitrogen). The FBP expression plasmid was constructed by inserting the FBP cDNA of Example 1 subcloned into EcoRI-XhoI sites of HA-tagged pcDNA3 (Invitrogen). After human embryonic kidney cells were transfected with the above prepared myc-(p38/JTV-1) plasmid and HA-FBP plasmid, they were cultured at 37° C. for 24 hours and proteins were then extracted from these cells by the same method as used in Example 1-2. The extracted proteins were western blotted with the anti-HA, anti c-myc and anti-myc antibodies (Santa Cruz Biotechnology, USA) (Kim T. et al., *J. Biol. Chem.*, 275: 21768–21772, 2000).

Figure 3:
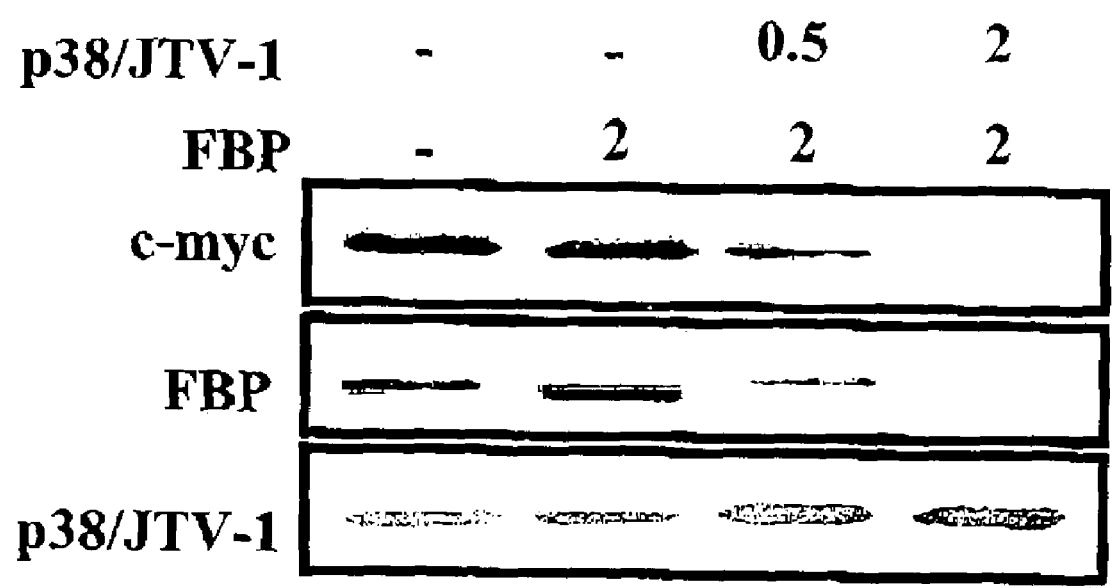
FIG. 3 is the western blotting results showing the change in FBP and c-myc according to the increase of the expression of p38/JTV-1 gene.

As a result, the expression levels of FBP and c-myc were decreased as the expression level of p38/JTV-1 was increased (FIG. 3).

Example 1-4 p38/JTV-1-Mediated Ubiquitination of FBP

To determine the ubiquitination of FBP, human embryonic kidney 293 cells (assigned from ATCC) were pretreated with 50 µg/ml of ALLN (N-acetyl-leucinal-leucinal-norleucinal) for three hours, to block 26S proteasome-mediated degradation of ubiquitinated proteins (Zhou M. et al., *J. Biol. Chem.*, 271, 24769–24775, 1996). After these cells had been transfected with 0, 1 and 2 µg/ml of the p38/JTV-1 expression plasmid of Example 1-3, respectively, proteins were extracted from these cells by the same method as used in Example 1-2 and then the extracted proteins was immunprecipitated using the anti-FBP antibody (Santa Cruz Biotechnology, USA). The immunoprecipitated proteins were western blotted with the anti-FBP antibody (Santa Cruz Biotechnology, USA) and the anti-ubiquitine antibody (Santa Cruz Biotechnology, USA) (Kim T. et al, *J. Biol. Chem.*, 275:21768–21772, 2000).

Also, the above 293 cells were co-transfected with the HA-ubiquitine plasmid (supplied by Dr. Sungho Ryu in Department of Life Science, Pohang University of Science and Technology, Korea) and myc-(p38/JTV-1) plasmid having a different amount each time. In other words, these cells were co-transfected with an HA-ubiquitine plasmid and 0, 1 and 2 µg/ml of myc-(p38/JTV-1) plasmid, respectively, and the obtained cells were then lysed with the RIPA buffer (10 mM Tris buffer pH 7.5, 0.1% SDS, 1 mM EDTA, 1% NP-40, 0.5% deoxycholate, 45 mM β-glycerolphosphate, 50 mM NaF, 1 mM dithiothreitol, 0.1 mM phenylmethylsulfonyl fluoride and 1 mM sodium orthovanadate) for 16 hours and immunoprecipitated with the anti-FBP antibody by the same method as used in Example 1-3. To determinate the ubiquitinated FBP, western blotting was conducted with the anti-HA antibody (Santa Cruz Biotechnology, USA) (Kim T. et al., *J. Biol. Chem.*, 275:21768–21772, 2000).

Figure 4A:
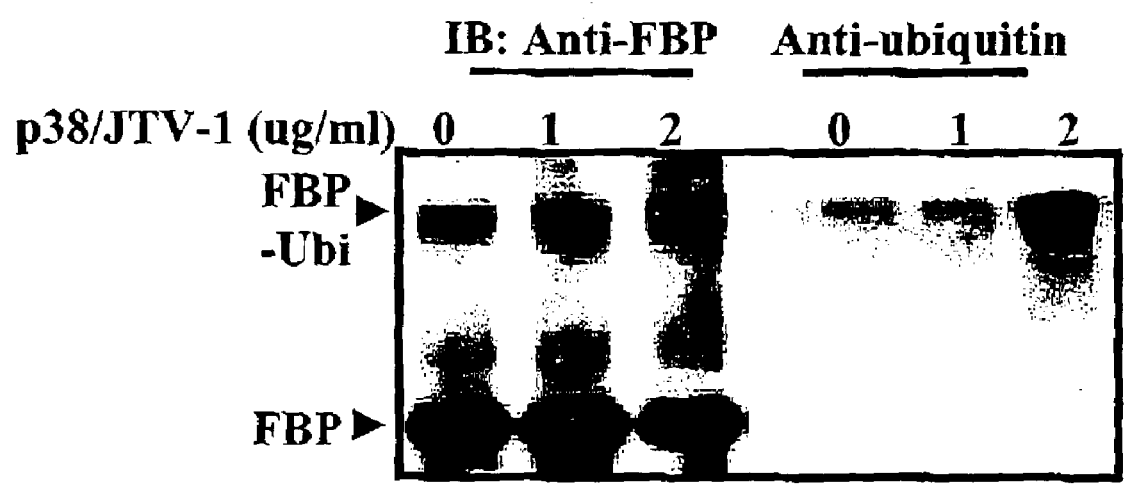
FIG. 4a is the immunoblotting results carried out using the anti-FBP antibody (left) and an anti-ubiquitine antibody (right) after the immunoprecipitation with the anti-FBP antibody, showing the degree of the ubiquitination of FBP according to the increase of the expression of a p38/JTV-1 gene (IB: immunoblotting, using the anti-FBP and the anti-ubiquitine antibodies, FBP-Ubi: ubiquitinated FBP).

As a result, the level of FBP was not affected by the change of p38/JTV-1 in the ALLN treated cells. This means that the degradation of FBP is mediated by 26S proteasome (FIG. 4a, left). Also, in addition to FBP, a high molecular weight bands were detected. To examine whether these bands are the ubiquitinated FBP, the proteins were immunoprecipitated with the anti-FBP antibody and immunoblotted with the anti-ubiquitine antibody. As a result, these bands were reacted with the anti-ubiquitine antibody. Accordingly, the high molecular weight bands could be confirmed as the ubiquitinated FBP (FIG. 4a, right).

Figure 4B:
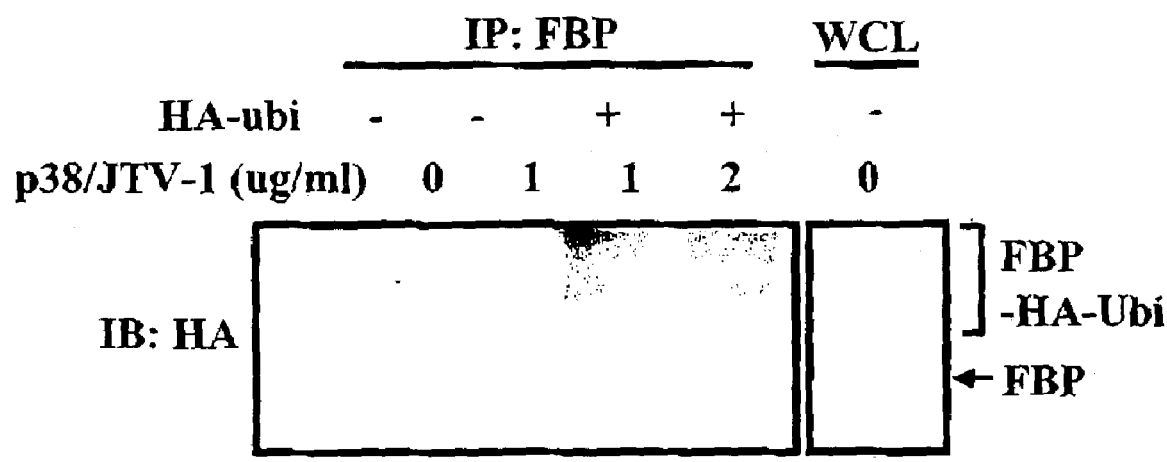
FIG. 4b shows the results obtained by transfecting cells with the plasmid encoding the HA-tagged ubiquitine gene and the plasmid encoding the p38/JTV-1 gene, immunoprecipitating them with the anti-FBP antibody and immunoblotting the precipitates with the anti-HA antibody (IP: immunoprecipitation, using the anti-FBP antibody, IB: immunoblotting, using the anti-HA antibody, WCL: whole cell lysate, not containing HA-ubiquitine plasmid, +: containing HA-ubiquitine plasmid).

In addition, the inventors expressed exogenous HA-ubiquitine and p38/JTV-1 in 293 cells with different levels of p38/JTV-1, and determined whether the ubiquitination of FBP is enhanced by p38/JTV-1. As a result, the ubiquitinated FBP was enhanced by the co-expression of p38/JTV-1 (FIG. 4b).

In conclusion, it could be seen that 26S proteasome was mediated in the degradation of FBP and p38/JTV-1 was also mediated in the ubiquitination and degradation of FBP.

Example 1-5

Effect of the Binding of p38/JTV-1 and FBP on the Ubiquitination of FBP and the Suppression of c-myc After p38/JTV-1 deletion fragments were constructed, it was examined whether these deletion fragments bind to FBP. cDNA encoding amino acids 1–312 (full length) of human p38/JTV-1 was constructed using primers shown in Table 2 below according to the same method as used in Example 1-1. cDNAs of the deletion fragments coding amino acids 1–161, amino acids 162–312 and amino acids 84–312 of human p38/JTV-1 were obtained by a PCR amplification using specific primer pairs and using the whole cDNA of p38/JTV-1 as a template. The specific primer pairs are as shown in Table 2 below. The PCR amplification was performed 30 cycle with 1 min. at 95° C., 1 min. at 60° C., 1 min. at 72° C. and 5 min. at 72° C. after the template DNA had been denaturation with 95° C. for 5 min.

TABLE 2

Primer Sequence Used for the Construction of p38/JTV-1 Deletion Fragments

| Amplified Site | Primer | Sequence | SEQ ID NO. |
|---|---|---|---|
| Amino acids 1–312 | Forward | ATGCCGATGTACCAGGTAAAG | 9 |
|  | Reverse | AAAAGGAGCCAGGTTTTCAC | 10 |
| Amino acids 1–161 | Forward | ATGCCGATGTACCAGGTAAAG | 9 |
|  | Reverse | CACGCTCTTGACCGAGGAGTG | 11 |
| Amino acids 162–312 | Forward | AAACCTTCTCAAGTGCTTTG | 12 |
|  | Reverse | AAAAGGAGCCAGGTTTTCAC | 10 |
| Amino acids 84–312 | Forward | AGATGCAGACTTGGATGTAAC | 13 |
|  | Reverse | AAAAGGAGCCAGGTTTTCAC | 10 |

The obtained cDNAs were each subcloned into EcoRI-XhoI sites of myc-tagged pcDNA3 (Invitorgen) The constructed plasmids were transfected together with the HA-FBP plasmid prepared in Example 1-3 above, into human embryonic kidney 293 cells. The transfected cells were lysed with the RIPA buffer for 16 hours after the transfection. The cell lysate was reacted with the anti-myc antibody at 4° C. for 3 hours. After a protein A-agarose bead had been added to the above reactant, the mixture was incubated further for 1 hour at 4° C. The bead was washed with lysis buffer four times. The precipitated proteins were analyzed by SDS-PAGE and then transferred onto nitrocellulose membranes. The immunoprecipitate was western blotted using the anti-myc antibody and anti-HA antibody (Kim T. et al., *J. Biol. Chem.*, 275:21768–21772, 2000). In the same manner, the whole cell lysate of the transfected 293 cells was western blotted with the anti-myc antibody to investigate whether or not p38/JTV-1 is expressed.

Also, to examine the effect of the p38/JTV-1 deletion fragments on the ubiquitination of FBP, the HA-ubiquitine plasmid and the plasmid expressing the p38/JTV-1 deletion fragment prepared in the above were transfected into 293 cells and then, immunoprecipitation and western blotting were performed using the anti-FBP antibody and anti-HA antibody according to the same method as above.

Further, the effect of the p38/JTV-1 deletion fragments on the expression of c-myc was determined by an RT-PCR. After the 293 cells had been transfected with a plasmid expressing the p38/JTV-1 deletion fragment for 24 hours, cell lysate was obtained using 500 μl of RNAsol and 200 μl of chloroform, and RNA was then extracted. After the obtained cell lysate was vortexed, it was incubated at 4° C. for 10 minutes and then separated by centrifugation at 4° C., 12000 rpm. To the supernatant was added 1 ml of isopropanoland the solution was incubated at −70° C. for 2 hours and centrifuged at 4° C., 12000 rpm for 30 minutes. The precipitate was dissolved with distilled water and measured the quantity and quality of RNA using a spectrophotometer. Also, after 1 μg of RNA extracted from the above cell lysate, 200 U of MoMuLV reverse transcriptase, 10 pM of random hexamer and 10 mM of dNTP were mixed, the mixture was subjected to reverse-transcription reaction annealing at 23° C. for 15 min., elongation at 42° C. for 60 min. and denaturation at 95° C. for 5 min, to thereby obtain cDNA. The obtained cDNA was amplified by PCR according to the same method as above and in this reaction, GADPH was used as the loading control and c-myc was used as the control. The primer pairs specific to p38/JTV-1 deletion cDNAs are as shown in Table 2 above and the primers for the amplification of GADPH and c-myc are as shown in Table 3 below. The finally amplified PCR products was electrophoresed on 2% agarose gel, which was then dyed with ethidium bromide and observed under UV.

TABLE 3

Primers of c-myc and GADPH Used in RT-PCR

| Primer | Sequence | SEQ ID NO. |
|---|---|---|
| c-myc forward primer | cagcagcctcccgcgacgat | 14 |
| c-myc reverse primer | agcctggtaggaggccagct | 15 |
| GADPH forward primer | ttccatggcaccgtcaaggc | 16 |
| GADPH reverse primer | cttggcagcgccagtagagg | 17 |

Figure 5A:
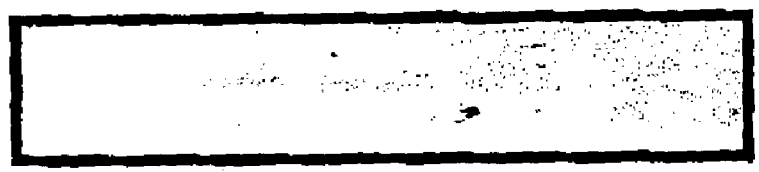
FIG. 5a shows the results obtained by transfecting 293 cells with the plasmid encoding the myc-tagged p38/JTV-1 deletion fragments and the plasmid encoding the HA-tagged FBP, immunoprecipitating them with the anti-myc antibody and assaying them by western blotting using the anti-FBP antibody (IP: immunoprecipitation, using the anti-myc antibody, WB: western blotting, using the anti-FBP antibody, WCL: whole cell lysate, arrow: peptides present in the vectors which bind to p38/JTV-1 when p38/JTV-1 is expressed)
Figure 5A:
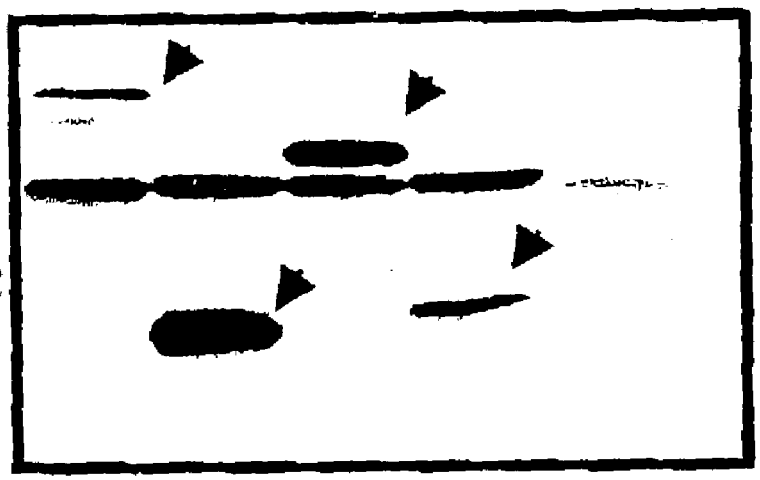
Figure 5B:
FIG. 5b shows the results obtained by transfecting 293 cells with the plasmid encoding the p38/JTV-1 deletion fragments and the plasmid encoding the HA-ubiquitine, immunoprecipitating them with the anti-FBP antibody and western blotting the precipitates with the anti-HA antibody (IP: immunoprecipitation, using the anti-FBP antibody, WB: western blotting, using the anti-HA antibody).
Figure 5C:
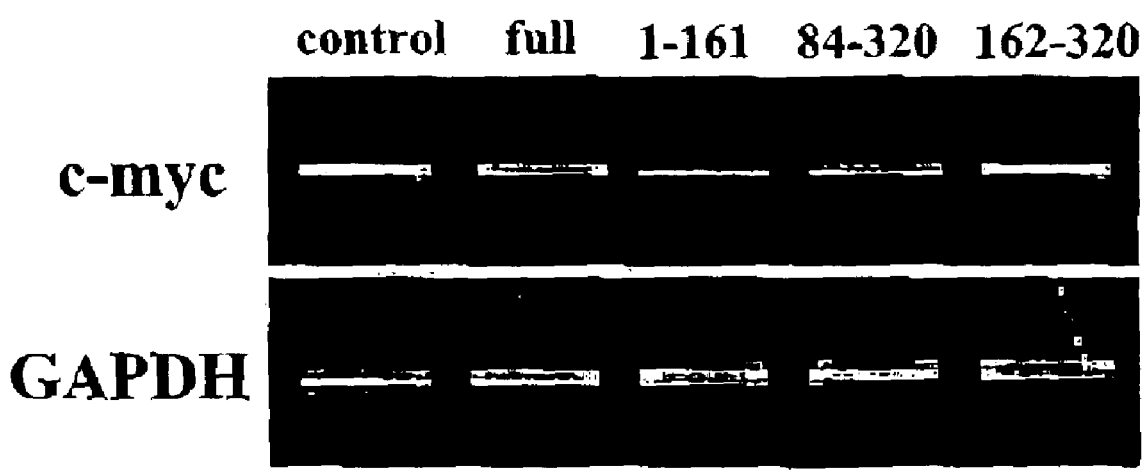
FIG. 5c is the RT-PCR assay results showing the effect of a p38/JTV-1 deletion fragments on the expression of c-myc (GAPDH; loading control, c-myc; control).

As a result, while the p38/JTV-1 fragments of amino acids 1–312 (full length), amino acids 1–161 and amino acids 84–312 bound to FBP, the p38/JTV-1 fragment of amino acids 162–312 did not. The western blotting of the whole cell lysate, which was not immunoprecipitated, with the anti-myc antibody showed that p38/JTV-1 was being expressed (FIG. 5a). Also, it could be seen that the ubiquitination of FBP was promoted only by the fragments of p38/JTV-1 capable of binding to FBP (FIG. 5b). In addition, the fragments of p38/JTV-1 bound to FBP, suppressed the c-myc expression and the deletion fragment of p38/JTV-1 not bound to FBP, did not suppress the c-myc expression (FIG. 5c). These results show that the binding of p38/JTV-1 to FBP is required for the ubiqutination of FBP and suppression of c-myc expression. (FIG. 5d).

Example 1-6

Effect of the Treatment of TGF-β 2 on the Expression of P38/JTV-1

A549 cells (lung epithelial carcinoma cells, assigned from ATCC) were treated with 2 ng/ml of TGF-β 2 (R&D) and western blotting was carried out using the anti p38/JTV-1, anti-FBP and anti c-myc antibodies (Santa Cruz Biotechnology, USA) according to the same method as used in Example 1-2. As the loading control, tubulin was used.

Figure 6:
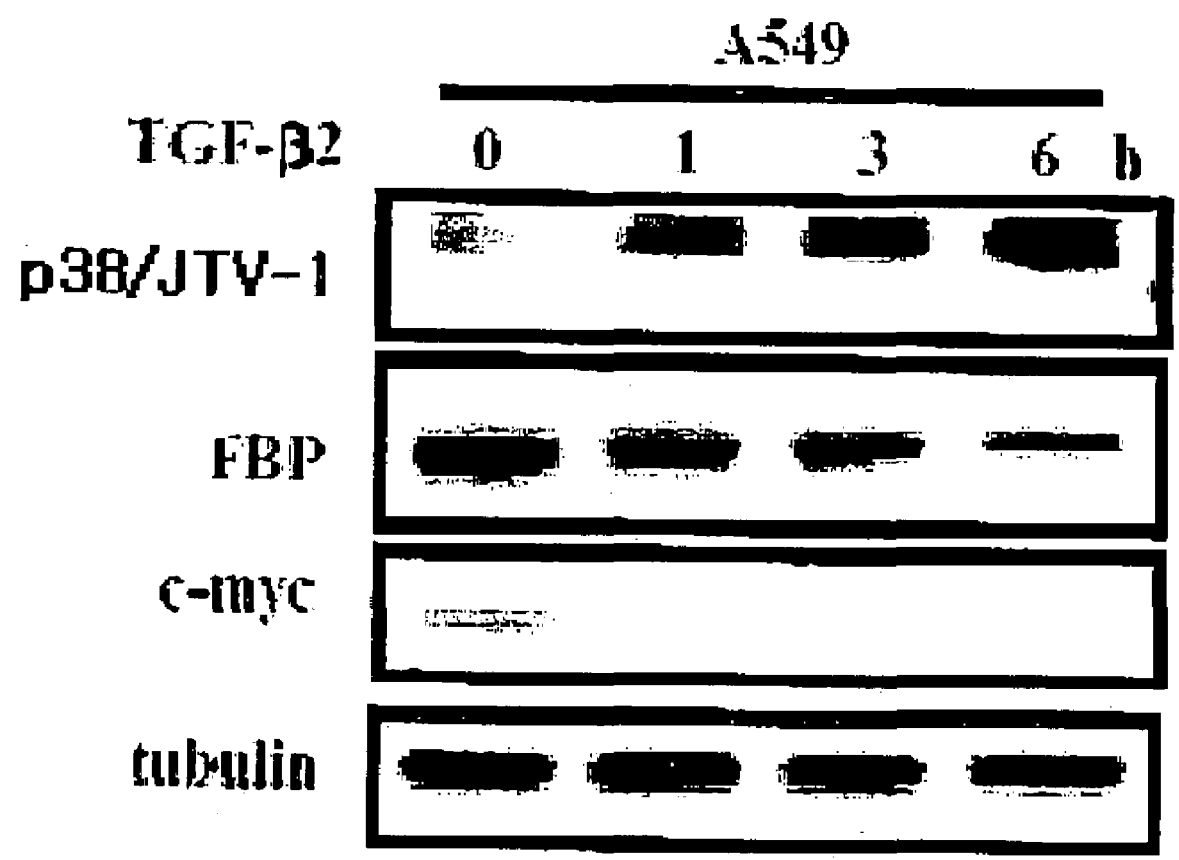
FIG. 6 is the western blotting results obtained using each specific antibody, showing the change in the expression level of p38/JTV-1, FBP and c-myc as time lapsed after the treatment of TGF-β 2 into A549 cells.
Figure 7:
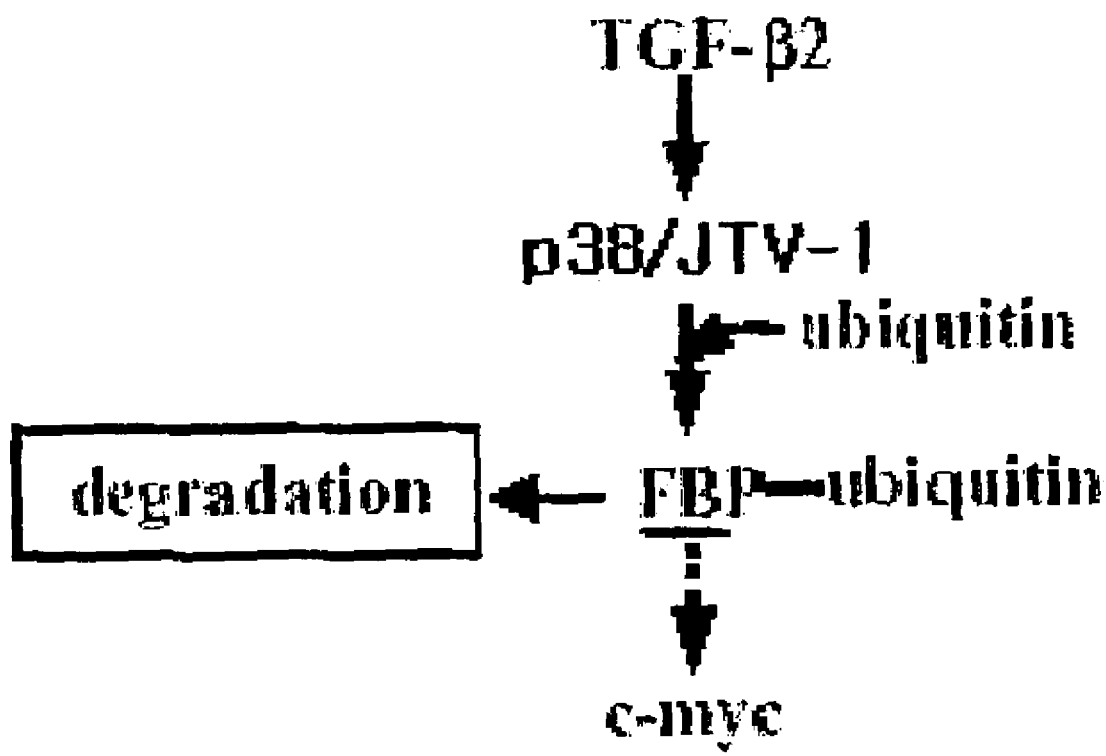
FIG. 7 is a scheme showing the regulation mechanism of c-myc by p38/JTV-1 (solid line: promotion, dotted line: suppression)

As a result, the expression level of p38/JTV-1 was increased by the treatment of TGF-β2. Also, it was observed that the p38/JTV-1 induced by TGF decreased the level of FBP and c-myc (FIG. 6). In conclusion, a new mechanism——TGF-β induces the expression of p38/JTV-1, which then binds to FBP and thus suppresses the expression of c-myc gene—could be revealed (FIG. 7).

Example 2

Regulation Mechanism of Apoptosis by the Interaction of p38/JTV-1 and PDK-1

Example 2-1

Activity of Phohphorylated AKT in Tissues Isolated from p38/JTV-1-Deficient Mouse The inventors examined the relationship between the p38/JTV-1 gene and AKT-PI3K pathway known for regulating apoptosis, in order to investigate the inhibitory mechanism of apoptosis by the p38/JTV-1 gene. For this, heart, liver, intestinal tract and brain tissues were isolated from wild type mouse and p38/JTV-1 deficient mouse. In addition, proteins were extracted from these tissues and analyzed by western blotting using the phospho-specific anti-AKT antibody (Santa Cruz Biotechnology, USA) and the phospho-specific anti-PI3K antibody (Santa Cruz Biotechnology, USA) according to the known methods (Kim T et al., *J. Biol. Chem.*, 275:21768–21772, 2000). Tubulin was used as the loading control In the same manner, in the embryonic fibroblast cells of wild type and p38/JTV-1 deficient mouse, the activity of phohphorylated AKT (p-AKT) and PI3K was examined. These embryonic fibroblast cells of p38/JTV-1 deficient mouse were obtained from 13.5-day embryo of p38/JTV-1 deficient mouse, from which the tissues was then chopped with knife and scissors and incubated with trypsin-EDTA solution at 37° C. for 1 hour. The culture solution was centrifuged at 1200 rpm for 5 min. to eliminate supernatants, and the precipitated tissue pellet was incubated in culture medium (RPMI-1640 containing 10% FBS) at 37° C. for one day. The cultured cells were recovered by washing and then used for experiments.

Figure 8A:
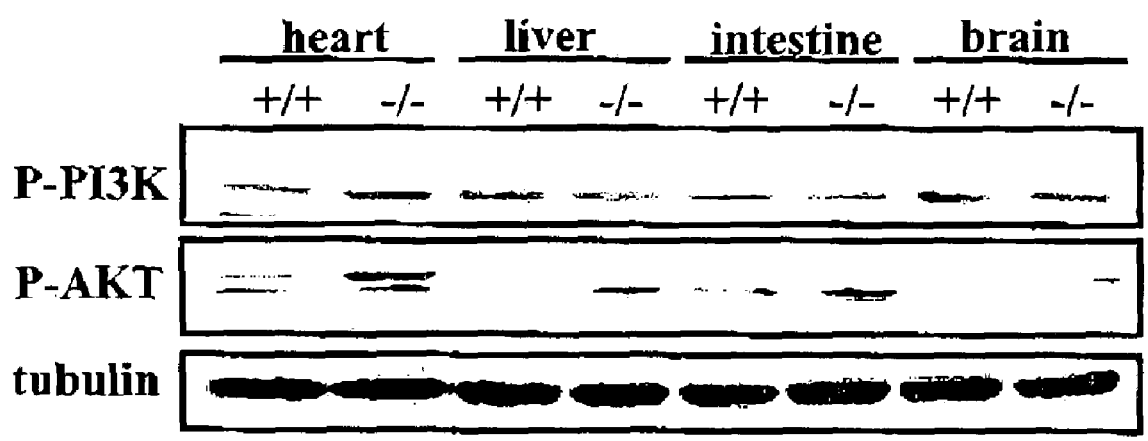
FIG. 8a is the western blotting results showing the expression level of phosphorylated PI3K and AKT in the tissues isolated from a wild type mouse and a p38/JTV-1-deficient mouse (+/+ wild type mouse, −/−p38/JTV-1 deficient mouse).
Figure 8B:
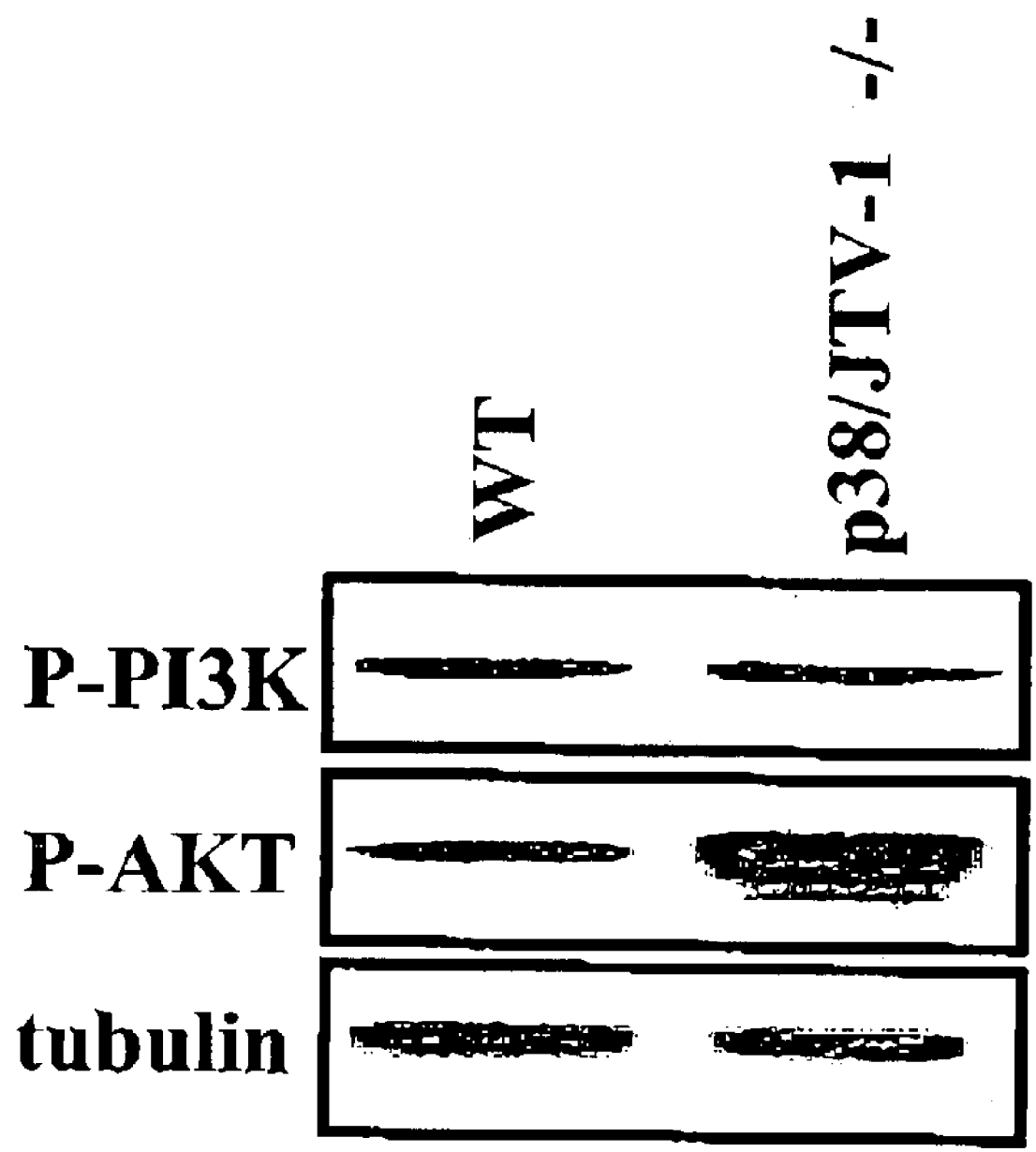
FIG. 8b is the western blotting results showing the expression level of phosphorylated PI3K and AKT in the embryonic fibroblast cells of a wild type mouse and a p38/JTV-1-deficient mouse (WT: wild type mouse embryonic fibroblast cells, p38/JTV-1 −/−: p38/JTV-1 deficient mouse embryonic fibroblast cells).

As a result, in all tissues isolated from the p38/JTV-1-deficient mouse, the expression level of PI3K and total AKT showed no difference from that of the wild type whereas the expression level of the phosphorylated AKT (p-AKT) was increased as compared with the wild type (FIG. 8a). The same results were obtained from the experiment using mouse embryonic fibroblast cells (FIG. 8b). From these results, it was assumed that p38/JTV-1 would be associated with the phosphorylation activity of AKT.

Example 2-2

Change in the Activity of the Phosphorylated AKT According to the Increase of the Expression of p38/JTV-1 and the Lapse of Time in Cancer Cells HCT116 cell line (human colorectal carcinoma cell line) was transfected with different amounts (0, 0.5 μg/ml, 1 μg/ml, 2 μg/ml) of the p38/JTV-1 expression plasmid of Example 1-3 and then, in the transfected cell line, the expression level of all factors associated with the AKT-PI3K pathway, that is, phosphorylated AKT, total AKT, PDK-1 and Bcl-2 family members were determined by the known western blotting (Kim T et al, *J. Biol. Chem.*, 275:21768–21772, 2000). Antibodies used in this western blotting were anti BID, anti BCL-XL and anti Bax antibodies (Santa Cruz Biotechnology, USA). In addition, the above cell line was transfected with 1 μg/ml of p38/JTV-1 expression plasmid and then, a change in the expression level of the phosphorylated AKT over the lapse of time was examined by western blotting.

Figure 9A:
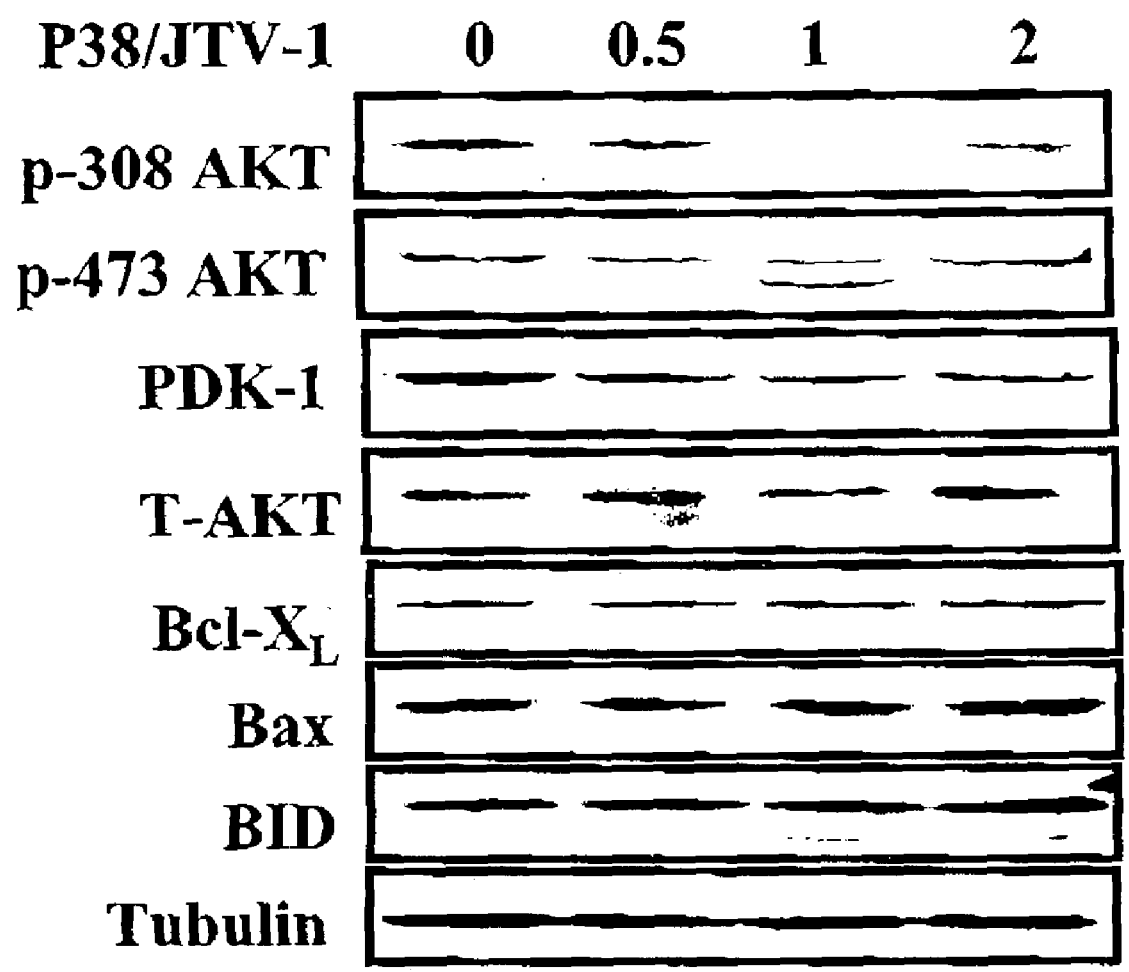
FIG. 9a is the western blotting results showing the expression level of phosphorylated AKT, PDK-1, total AKT and Bcl-2 family members according to the increase of the expression level of p38/JTV-1 in the HCT 116 cell line.
Figure 9B:
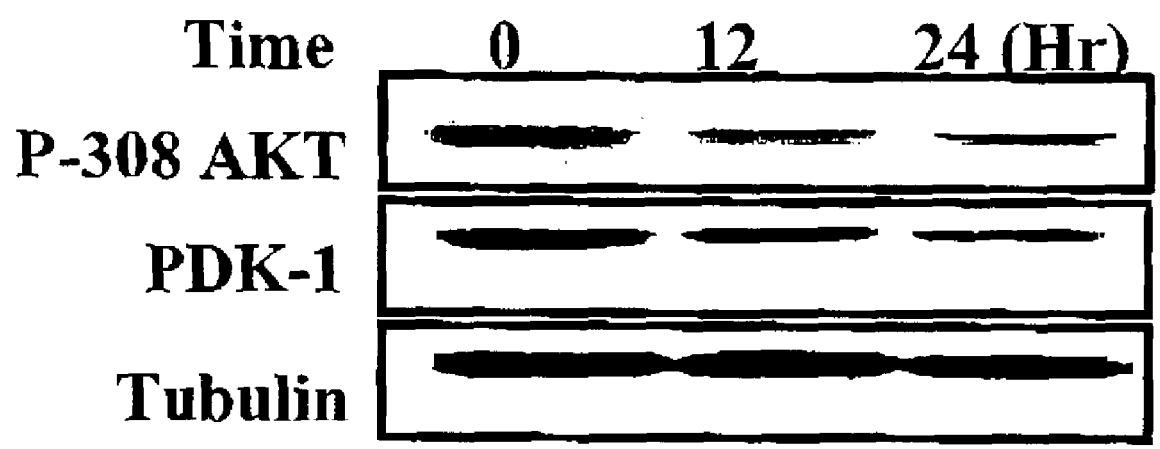
FIG. 9b is the western blotting results showing the expression level of phosphoylated AKT and PDK-1 in the HCT116 cell line transfected with a p38/JTV-1 expression vector as time lapsed.

As a result, when the expression level of p38/JTV-1 was increased, the expression level of the phosphorylated AKT (p-308 and p-473) was decreased. On the other hand, Bcl-2 family members were not affected by the expression level of p38/JTV-1, and the expression level of total AKT showed no change. Also, the expression level of PDK-1 showed a tendency of decreasing according to the increase of the intracellular expression level of p38/JTV-1 (FIG. 9a). The phosphorylation inhibitory activity of AKT by p38/JTV-1 was increased in time-dependent manner (FIG. 9b). These results supported that p38/JTV-1 is a novel negative regulator on activation of AKT.

Example 2-3

Analysis of the Interaction Between p38/JTV-1 and PDK-1

Interaction between p38/JTV-1 and PDK-1 was examined through immunoprecipitation. HCT116 cell line was transfected with an HA-(p38/JTV-1) expression plasmid and immunoprecipitation was then performed using the IgG, anti PDK-1, anti-AKT and anti-PI3K antibodies. The immunoprecipitates were analyzed using western blotting with the anti-myc, anti PDK-1 and anti-PI3K antibodies (Santa Cruz Biotechnology, USA) (Kim T. et al., *J. Biol. Chem.*, 275: 21768–21772, 2000).

Figure 10:
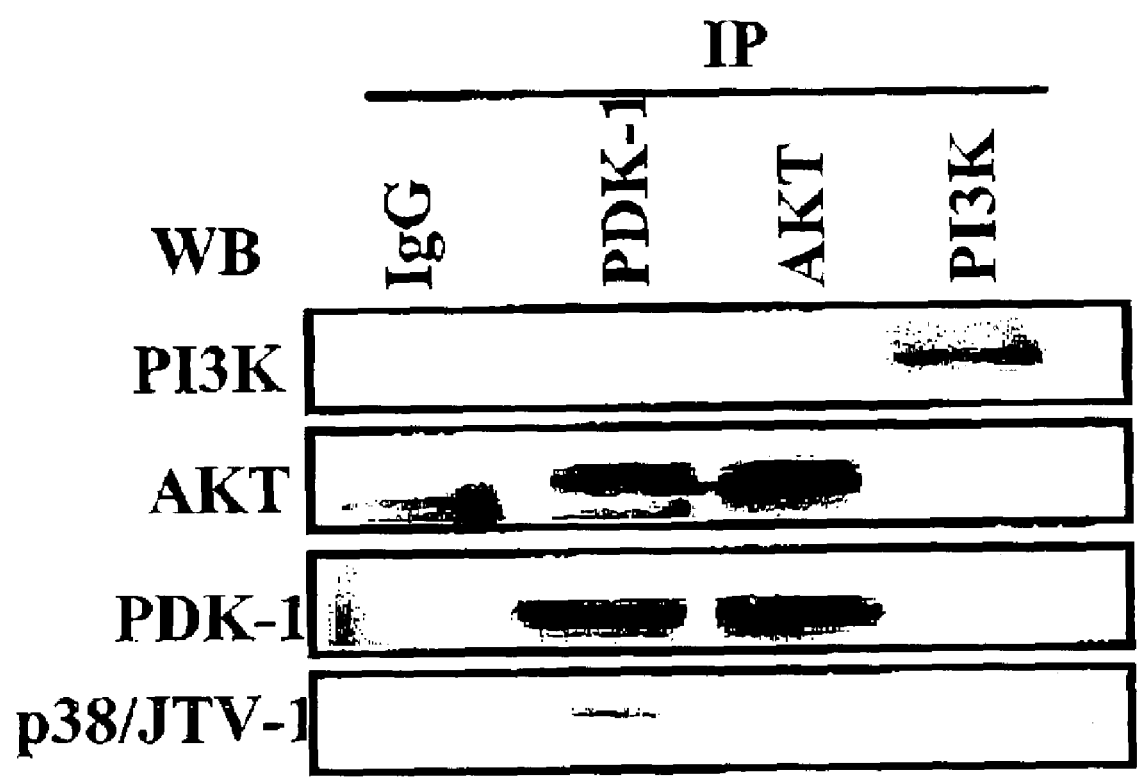
FIG. 10 is the immunoprecipitation results showing the interaction between p38/JTV-1 and PDK-1 (IP: immunoprecipitation, using the anti-IgG, anti PDK-1, anti-AKT and anti-PI3K antibodies, WB: western blotting, using the anti-PI3K, anti-AKT, PDK-1 and anti-p38/JTV-1 antibodies).

As a result, the strong interaction between p38/JTV-1 and PDK-1 was observed. On the other hand, p38/JTV-1 and P13K observed no interaction (FIG. 10).

Example 2-4

Interaction Between PDK-1 Deletion Fragments and 138/JTV-1

Since PDK-1 has two functional motives that kinase domain (KH) that is responsible for activation of AKT and plecstrin homologue (PH) domain that is important for membrane anchoring and activation by IP3, the inventors examined the interaction between PDK-1 deletion fragments and p38/JTV-1.

The nucleotide sequence of cDNA encoding PDK-1 was known (Gene Bank Accession No. NM_003902), and the plasmids expressing each PDK-1 deletion fragment, that is, the plasmids expressing amino acids J-556, amino acids 1–449, amino acids 52–341, amino acids 52–556, amino acids 156–556 and amino acids 244–556 of PDK-1 (FIG. 11a) were supplied by Dr. Naoya Fijita in Institute of Molecular and cellular bioscience, University of Tokyo. After human embryonic kidney cells were transfected with each plasmid, the cells were cultured and the cell lysates were obtained and then, they were immunoprecipitated with the anti-FLAG antibody and analyzed by western blotting using the anti p38/JTV-1 antibody and anti-FLAG antibody (Santa Cruz Biotechnology, USA) (Kim T. et al., *J. Biol. Chem.*, 275:21768–21772, 2000).

Figure 11B:
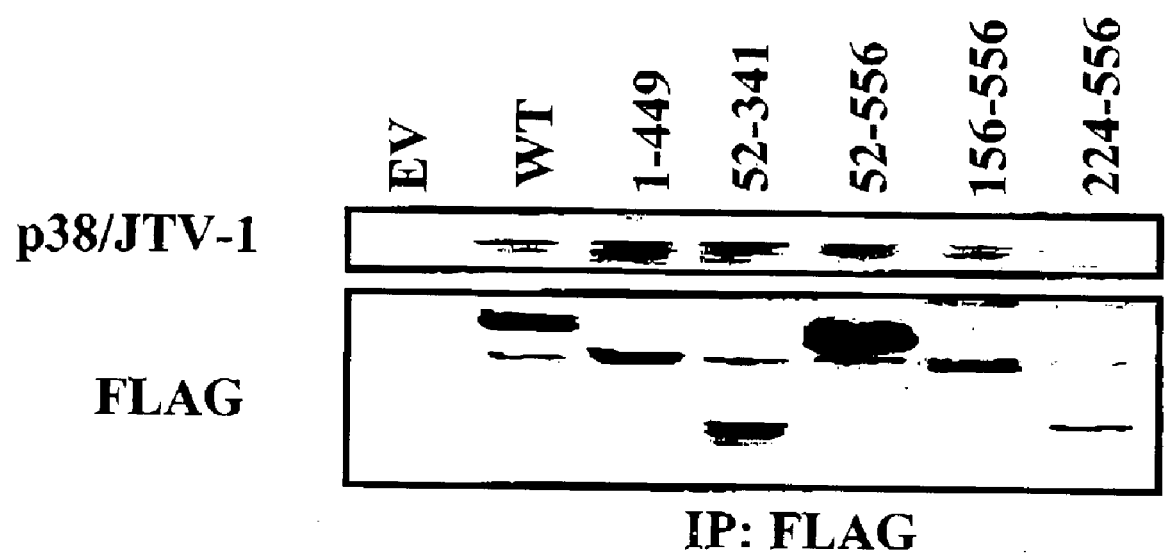
FIG. 11b is the western blotting results showing the interaction between PDK-1 deletion fragments and p38/JTV-1 (EV: cells into which pcDNA is introduced, WT: wild-type cells, IP: immunoprecipitation, using the anti-FLAG antibody).

As a result, comparing with strong interaction between p38/JTV-1 and PDK-1 full-length of fragment, deletion of kinase domain abolished the interacting ability of PDK-1 and p38/JTV-1. In contrast, the deletion of the PH domain did not affect the interaction with p38/JTV-1 (FIG. 11b). Therefore, from the fact that the PDK-1 fragment, which is deficient in the kinase domain (KH) activating AKT, showed no interaction with p38/JTV-1, it could be seen that p38/

JTV-1 binds to the KH domain of PDK-1 and thus suppresses PDK-1 from activating AKT.

Example 2-5

Change in the Expression Level of p38/JTV-1 According to the Treatment of Death Ligands Under the presence of death ligands, a change in the expression level of p38/JTV-1 was examined. HCT116 cells (human colorectal carcinoma, assigned from ATCC) into which the p38/JTV-1 expression plasmid is introduced were treated with death ligands for promoting apoptosis by binding to a death receptor, one of the signal transduction pathways for regulating apoptosis, and the expression level of p38/JTV-1 was examined. As death ligands, 500 ng/ml of FasL or 10 ng/ml of TNF were used, and after they had been treated into the above cell line for 6 hours, the expression level of p38/JTV-1, p-AKT, total AKT and PDK-1 was examined by western blotting using each specific antibody (Santa Cruz Biotechnology, USA) Tubulin was used as the loading control. Also, after HCT116 cells into which the p38/JTV-1 expression plasmid is introduced had been treated with death ligands, respectively, the cell lysates were immunoprecipitated with the anti PDK-1 antibody and then western blotted with the p38/JTV-1 antibody.

Figure 12A:
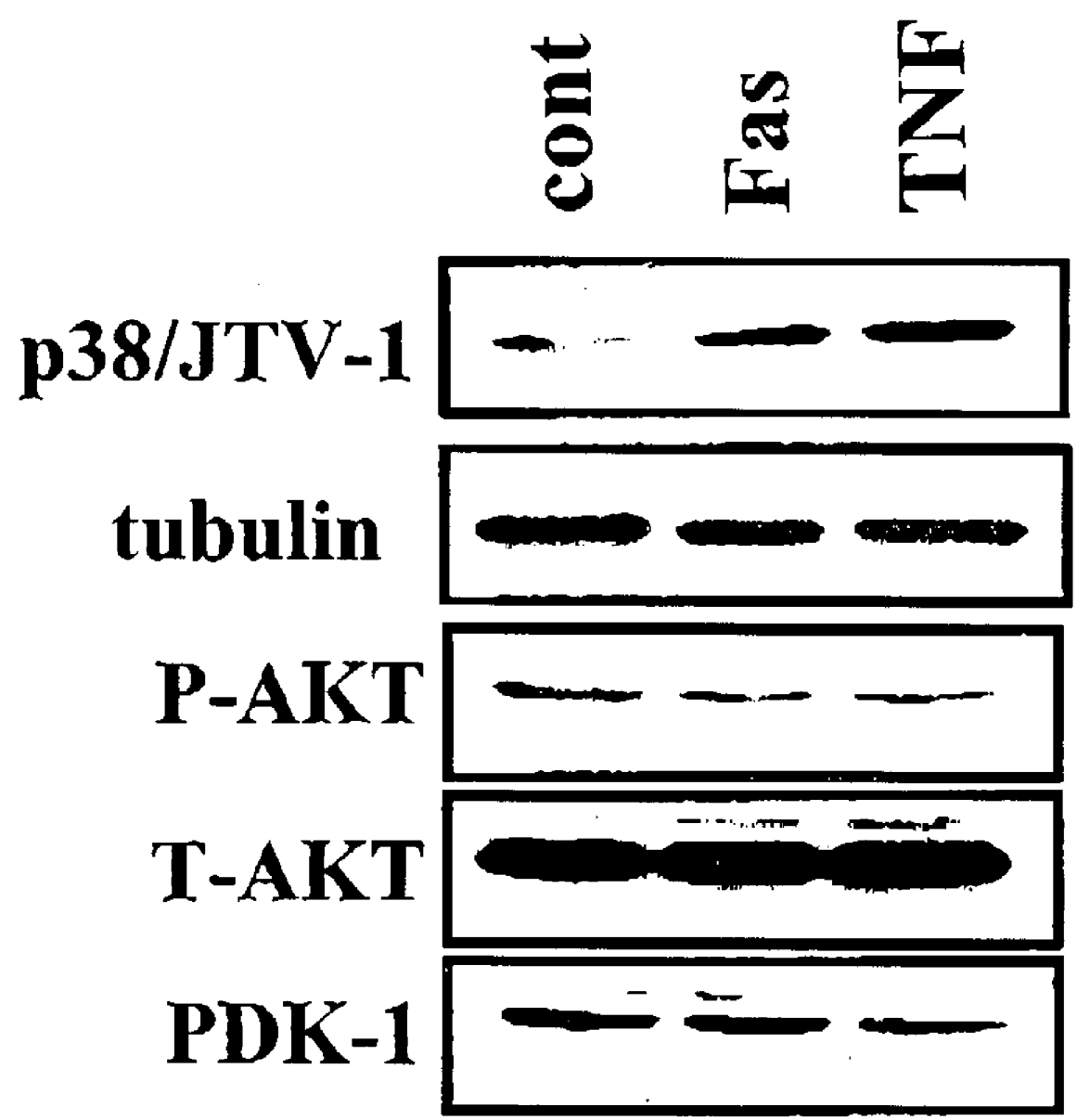
FIG. 12a is the western blotting results showing the expression level of phosphorylated AKT and the change in the expression of p38/JTV-1 according to the treatment of death ligands.
Figure 12B:
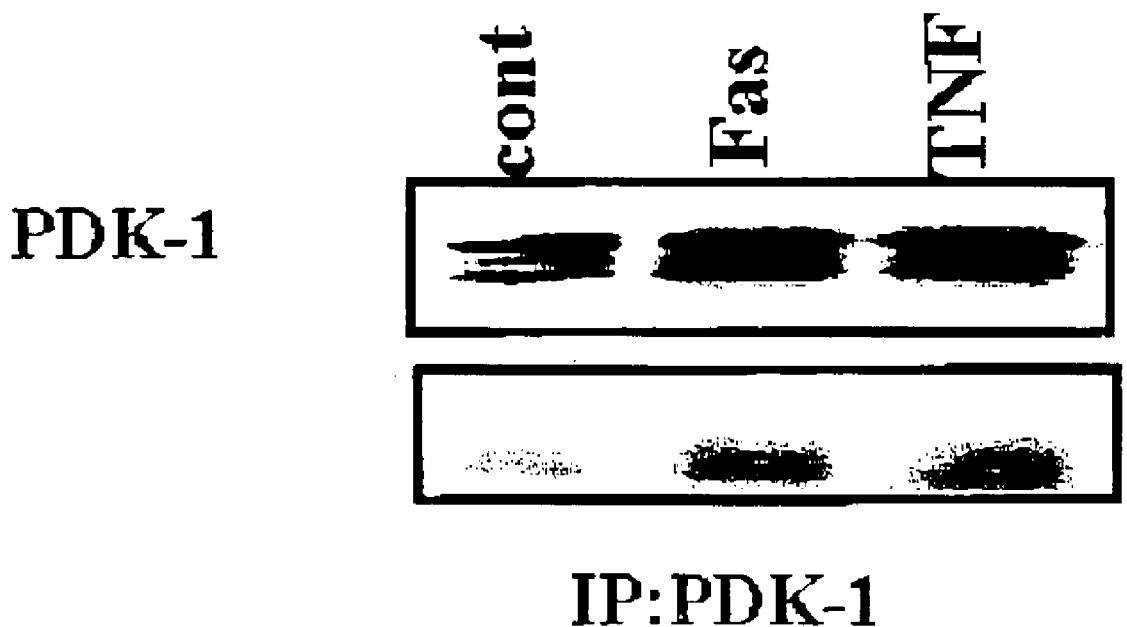
FIG. 12b is the immunoprecipitation assay results showing the change in the interaction between p38/JTV-1 and PDK-1 according to the treatment of death ligands (IP: immunoprecipitation, treatment with the anti PDK-1 antibody, control: no treatment with death ligands).

As a result, when FasL and TNF were treated, the expression of p38/JTV-1 was increased and the expression level of p-AKT was decreased as compared with the case where no death ligand was treated (FIG. 12a). Also, the interaction between p38/JTV-1 and PDK-1 was increased according to the treatment of the death ligands (FIG. 12b).

Example 3

Confirmation of the Use of p38/JTV-1 as Anticancer Agent

Example 3-1

Effect of p38/JTV-1 on the Proliferation of Cancer Cell Lines

After cancer cell lines had been transfected with the p38/JTV-1 expression plasmid, they were cultured for 48 hours and the proliferation of cells was examined using the radioactive thymidine. As cancer cell lines, HCT116 (human colorectal carcinoma), HeLa (cervical cancer) and A549 (lung epithelial carcinoma) cells were purchased from ATCC (American type culture collection) The transfected cells were transferred onto new media containing luCi[3H] thymidine and cultured further for 4 hours. The cultured cells were washed, collected, and then lysed with the RIPA buffer. The amount of the incorporated thymidine was quantified using the liquid scintillation counter, and DNA synthesis rate was calculated from the amount of the incorporated thymidine. The relative DNA synthesis rate in the experimental groups was calculated from the DNA synthesis rate of control group defined as 1.

Figure 14:
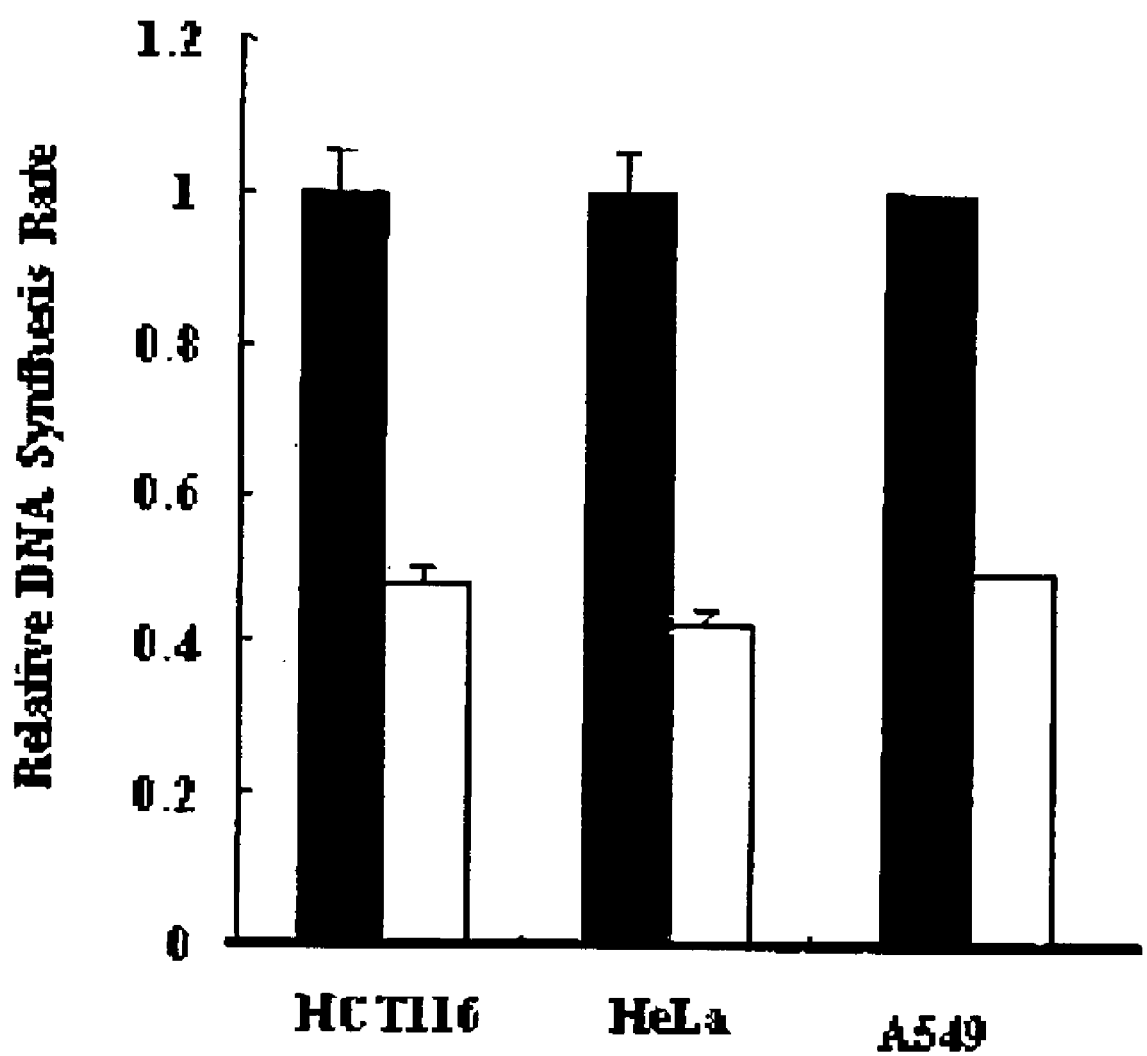
FIG. 14 shows the effect of p38/JTV-1 on the proliferation of cells in cancer cell lines (HCT116: human colorectal carcinoma, HeLa: cervical cancer, A549: lung epithelial carcinoma).

As a result, the p38/JTV-1 significantly suppressed the proliferation of HCT116 (human colorectal carcinoma), HeLa (cervical cancer) and A549 (lung epithelial carcinoma) cells (FIG. 14).

Example 3-2

Change in Apoptosis in Cancer Cell Lines into which p38/JTV-1 is Introduced

After HeLa cells (cervical cancer cell line) had been transfected with the p38/JTV-1 expression plasmid for 24 hours, they were cultured additionally for 24 hours after the addition of 500 ng/ml of FasL and then, the release of cytochrom C and the cells in which apoptosis occurred were determined. Also, HeLa cells were treated with pcDNA containing no p38/JTV-1 gene in the same condition as above and they were then compared with the case where the p38/JTV-1 gene is introduced. The release of cytochrome C, a physiological change occurring in the cells showing apoptosis, is exported from mitochondria due to the loss of the potential difference of mitochondria, and has a function of activating caspase 9 and apaf-1. The number of cells where apoptosis occurs was measured by trypan blue dye exclusion (Rao M, Kumar et al., *J. Biochem.* (Tokyo), 125(2): 383–90, 1999)., and the release of cytochrome C in mitochondria was detected by western blotting of cytochrome C within cytoplasm after the elimination of microorganelle fractions. In other Words, the HeLa cells were cultured with the storage solution (hypotonic solution, NaCl 10 ml, $MgCl_2$ 1.5 mM, Tris-Cl, pH 7.5) and plasma membranes were disrupted using glass dounce homogenizer under the MS buffer (mannitol 525 mM, sugar 175 mM, Tris-Cl 175 mM, EDTA 2.5 mM, pH 7.5). The cells from which the plasma membranes were removed were centrifuged at 1300 rpm at 4° C. for 5 min. to thereby eliminate nucleus. Then, they were ultra-centrifuged at 17000 rpm at 4° C. for 15 min. to separate them into cytoplasms and microorganells and the latter was eliminated. The remaining fraction was electrophoresed on SDS-PAGE and western blotted according to the known methods to thereby determine the release degree of cytochrome C (Marsden V. S. et al., *Nature* 419: 634, 2002). As a loading control, tubulin was used.

Figure 15A:
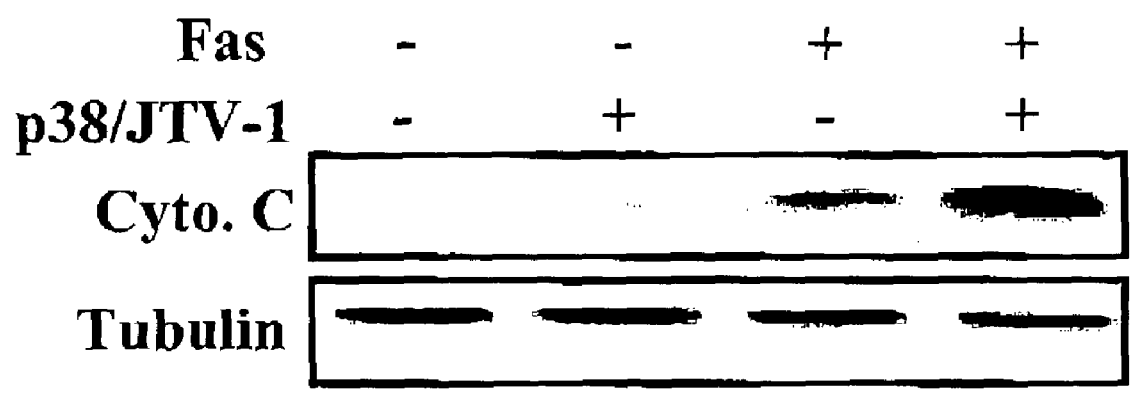
FIG. 15a is the western blotting results showing the release of cytochrome C according to the treatment of death ligands and the introduction of p38/JTV-1 into cancer cell lines (−: not added, +: added).
Figure 15B:
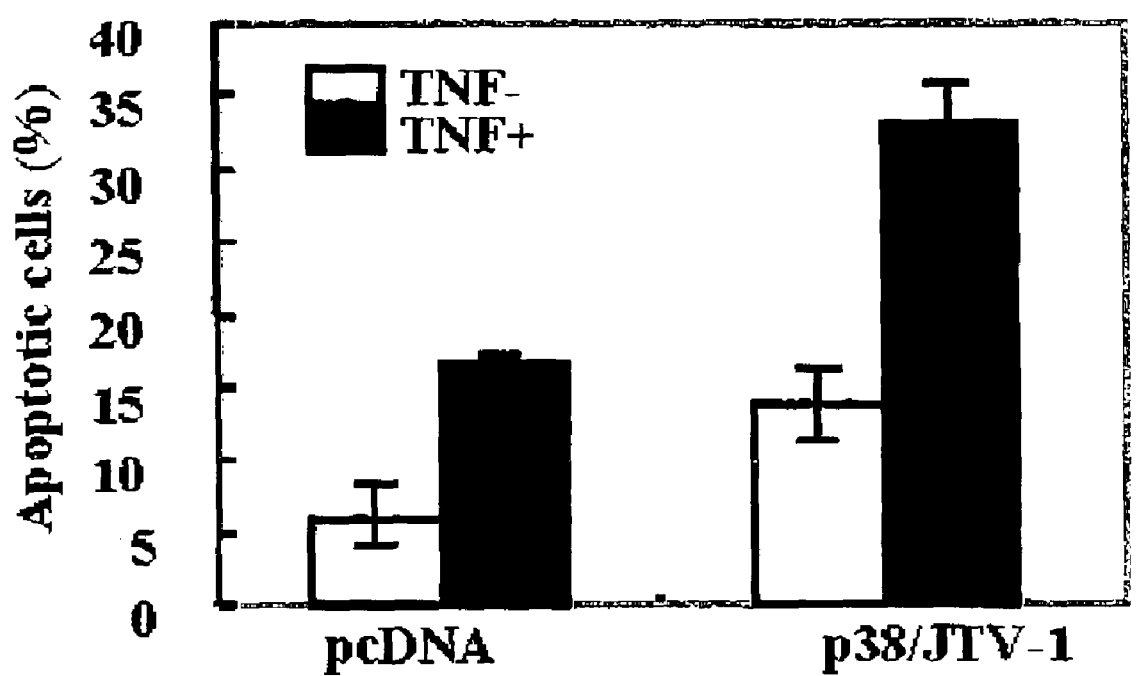
FIG. 15b shows the number of cells killed by apoptosis according to the treatment of death ligands and the introduction of p38/JTV-1 into cancer cell lines, by terms of percentage with regard to the total cell numbers (TNF−: no treatment with TNF, TNF+: treatment with A, pcDNA: cells into which pcDNA is introduced, p38/JTV-1 cells into which p38/JTV-1 gene is introduced).

As a result, when the p38/JTV-1 gene introduced into cancer cell line, the release of cytochrome C and apoptosis were increased as compared with the case where the p38/JTV-1 gene was not introduced. Also, apoptosis was increased by the treatment of the death ligand, INF (FIG. 15a and FIG. 15b). This shows that the p38/JTV-1 can be used as an anticancer agent by promoting apoptosis.

INDUSTRIAL APPLICABILITY

As described in the above, the treatment method according to the invention can be usefully used to treat cancer through the mechanism of suppressing the proliferation of cancer cells by binding to FBP (FUSE-binding protein) and thereby promoting the ubiquitination of FBP to downregulate c-myc gene, which is a proto-oncogene, and the mechanism of promoting the apoptosis of cells by binding to PDK-1 (phosphoinositide-dependent kinase) and thereby inhibiting the phosphorylation of AKT (serine/threonine kinase). Also, p38/JTV-1 can be used as a target for screening of new anticancer agents, by virtue of such regulation mechanisms of p38/JTV-1.

The invention claimed is:

1. A method for downregulating expression of the oncogene c-myc, which comprises administering an effective amount of an expression vector comprising an isolated nucleic acid encoding the p38/JTV-1 protein comprising the amino acid sequence of SEQ ID NO: 4 to a patient.

2. A method for promoting apoptosis of a cancer cell, which comprises administering an effective amount of an expression vector comprising an isolated nucleic acid encoding the p38/JTV-1 protein comprising the amino acid sequence of SEQ ID No. 4 to a patient.

3. A method for treating human cancer, which comprises administering the effective amount of an expression vector comprising an isolated nucleic acid encoding the p38/JTV-1 protein comprising the amino acid seciuence of SEQ ID NO: 4.

4. The method for treating human cancer according to claim 3, wherein said nucleic acid comprises nucleotide sequence represented by SEQ ID NO. 1.

5. The method for treating cancer according to claim 3, wherein said expression vectors are plasmids or viral vectors.

6. The method for treating human cancer according to claim 5, wherein said plasmid is pcDNA3.

7. The method for treating human cancer according to claim 5, wherein said viral vector is an adenovirus vector.

8. The method for treating human cancer according to claim 3, said cancer is selected from breast cancer, large intestinal cancer, lung cancer, small cell lung cancer, stomach cancer, liver cancer, blood cancer, bone cancer, pancreatic cancer, skin cancer, head or neck cancer, cutaneous or intraocular melanoma, uterine sarcoma, ovarian cancer, rectal cancer, anal cancer, colon cancer, fallopian tube carcinoma, endometrial carcinoma, cervical cancer, vulval cancer, vaginal carcinoma, Hodgkin's disease, esophageal cancer, small intestine cancer, endocrine cancer, thyroid cancer, parathyroid cancer, adrenal cancer, soft tissue tumor, urethral cancer, penile cancer, prostate cancer, chronic or acute leukemia, lymphocytic lymphoma, bladder cancer, kidney cancer, ureter cancer, renal cell carcinoma, renal pelvic carcinoma, CNS tumor, primary CNS lymphoma, bone marrow tumor, brain stem nerve gliomas, pituitary adenoma, or a combination thereof.

* * * * *